(12) United States Patent
Orlando et al.

(10) Patent No.: US 8,679,766 B2
(45) Date of Patent: Mar. 25, 2014

(54) E-CADHERIN AS A BIOMARKER OF GASTROESOPHAGEAL REFLUX DISEASE

(75) Inventors: Roy C. Orlando, Efland, NC (US);
Biljana Jovov, Chapel Hill, NC (US);
Nelia A. Tobey, Raleigh, NC (US);
Geraldine S. Orlando, Efland, NC (US);
Zorka Djukic, Durham, NC (US)

(73) Assignee: The University of North Carolina at Chapel Hill, Chapel Hill, NC (US)

( * ) Notice: Subject to any disclaimer, the term of this patent is extended or adjusted under 35 U.S.C. 154(b) by 54 days.

(21) Appl. No.: 13/305,790

(22) Filed: Nov. 29, 2011

(65) Prior Publication Data

US 2012/0094318 A1 Apr. 19, 2012

Related U.S. Application Data

(63) Continuation-in-part of application No. PCT/US2010/036634, filed on May 28, 2010.

(60) Provisional application No. 61/182,400, filed on May 29, 2009.

(51) Int. Cl.
*G01N 33/53* (2006.01)

(52) U.S. Cl.
USPC .......................................................... 435/7.1

(58) Field of Classification Search
None
See application file for complete search history.

(56) References Cited

U.S. PATENT DOCUMENTS

| 6,743,820 B2 | 6/2004 | Hudson et al. |
| 2005/0244517 A1 | 11/2005 | Hall et al. |
| 2007/0178510 A1 | 8/2007 | Chandrasoma |
| 2008/0103169 A1 | 5/2008 | Phillips |

FOREIGN PATENT DOCUMENTS

| WO | WO 02-10767 | 2/2002 |
| WO | WO 2006-083390 | 8/2006 |
| WO | WO 2008-069608 | 6/2008 |
| WO | WO 2010-138851 | 12/2010 |

OTHER PUBLICATIONS

International Search Report and Written Opinion of International Application No. PCT/US2010/036634, mailed Feb. 21, 2011 (12 pages).
Johnston et al. "Cell Biology of Laryngeal Epithelial Defenses in Health and Disease: Further Studies" *Ann Otol Rhinol Laryngol* 112(6):481-491 (2003).

*Primary Examiner* — Michael Pak
(74) *Attorney, Agent, or Firm* — Myers Bigel Sibley & Sajovec, PA

(57) ABSTRACT

The present invention provides methods of diagnosing and identifying subjects as having GERD comprising detecting E-cadherin fragments in a biological sample from the subject. The invention further provides methods for identifying subjects as having heartburn that is responsive to proton pump inhibitor therapy and subjects having an increased likelihood of a rapid relapse of GERD after reducing the dosage of PPIs or terminating PPI therapy. In addition, the present invention provides methods for monitoring the healing of erosive and nonerosive esophagitis of GERD without the need for esophagogastroduodenoscopy or esophagogastroduodenoscopy and biopsy, respectively.

3 Claims, 13 Drawing Sheets

FIG. 1

```
Met Gly Pro Trp Ser Arg Ser Leu Ser Ala Leu Leu Leu Leu Leu Gln
1               5                   10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45

Gly Arg Val Leu Gly Arg Val Asn Phe Glu Asp Cys Thr Gly Arg Gln
    50                  55                  60

Arg Thr Ala Tyr Phe Ser Leu Asp Thr Arg Phe Lys Val Gly Thr Asp
65                  70                  75                  80

Gly Val Ile Thr Val Lys Arg Pro Leu Arg Phe His Asn Pro Gln Ile
                85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro Pro His
            115                 120                 125

Gln Ala Ser Val Ser Gly Ile Gln Ala Glu Leu Leu Thr Phe Pro Asn
    130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
            165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
            195                 200                 205

Arg Glu Thr Gly Trp Leu Lys Val Thr Glu Pro Leu Asp Arg Glu Arg
    210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
            245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
            275                 280                 285

Ala Asp Asp Asp Val Asn Thr Tyr Asn Ala Ala Ile Ala Tyr Thr Ile
    290                 295                 300
```

FIG. 1 (Cont.)

```
Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
            325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
            355                 360                 365

Asn Asp Asn Pro Pro Ile Phe Asn Pro Thr Thr Tyr Lys Gly Gln Val
    370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
            405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
    450                 455                 460

Ser Leu Thr Thr Ser Thr Ala Thr Val Thr Val Asp Val Leu Asp Val
465                 470                 475                 480

Asn Glu Ala Pro Ile Phe Val Pro Pro Glu Lys Arg Val Glu Val Ser
            485                 490                 495

Glu Asp Phe Gly Val Gly Gln Glu Ile Thr Ser Tyr Thr Ala Gln Glu
            500                 505                 510

Pro Asp Thr Phe Met Glu Gln Lys Ile Thr Tyr Arg Ile Trp Arg Asp
            515                 520                 525

Thr Ala Asn Trp Leu Glu Ile Asn Pro Asp Thr Gly Ala Ile Ser Thr
        530                 535                 540

Arg Ala Glu Leu Asp Arg Glu Asp Phe Glu His Val Lys Asn Ser Thr
545                 550                 555                 560

Tyr Thr Ala Leu Ile Ile Ala Thr Asp Asn Gly Ser Pro Val Ala Thr
            565                 570                 575

Gly Thr Gly Thr Leu Leu Leu Ile Leu Ser Asp Val Asn Asp Asn Ala
            580                 585                 590

Pro Ile Pro Glu Pro Arg Thr Ile Phe Phe Cys Glu Arg Asn Pro Lys
            595                 600                 605
```

FIG. 1 (Cont.)

```
Pro Gln Val Ile Asn Ile Ile Asp Ala Asp Leu Pro Pro Asn Thr Ser
    610             615             620
Pro Phe Thr Ala Glu Leu Thr His Gly Ala Ser Ala Asn Trp Thr Ile
625             630             635                         640
Gln Tyr Asn Asp Pro Thr Gln Glu Ser Ile Ile Leu Lys Pro Lys Met
                645             650                 655
Ala Leu Glu Val Gly Asp Tyr Lys Ile Asn Leu Lys Leu Met Asp Asn
            660             665                 670
Gln Asn Lys Asp Gln Val Thr Thr Leu Glu Val Ser Val Cys Asp Cys
        675             680             685
Glu Gly Ala Ala Gly Val Cys Arg Lys Ala Gln Pro Val Glu Ala Gly
    690             695             700
Leu Gln Ile Pro Ala Ile Leu Gly Ile Leu Gly Gly Ile Leu Ala Leu
705             710             715                         720
Leu Ile Leu Ile Leu Leu Leu Leu Leu Phe Leu Arg Arg Arg Ala Val
                725             730             735
Val Lys Glu Pro Leu Leu Pro Pro Glu Asp Asp Thr Arg Asp Asn Val
            740             745             750
Tyr Tyr Tyr Asp Glu Glu Gly Gly Gly Glu Glu Asp Gln Asp Phe Asp
            755             760             765
Leu Ser Gln Leu His Arg Gly Leu Asp Ala Arg Pro Glu Val Thr Arg
    770             775             780
Asn Asp Val Ala Pro Thr Leu Met Ser Val Pro Arg Tyr Leu Pro Arg
785             790             795                         800
Pro Ala Asn Pro Asp Glu Ile Gly Asn Phe Ile Asp Glu Asn Leu Lys
                805             810                 815
Ala Ala Asp Thr Asp Pro Thr Ala Pro Pro Tyr Asp Ser Leu Leu Val
            820             825                 830
Phe Asp Tyr Glu Gly Ser Gly Ser Glu Ala Ala Ser Leu Ser Ser Leu
        835             840             845
Asn Ser Ser Glu Ser Asp Lys Asp Gln Asp Tyr Asp Tyr Leu Asn Glu
    850             855                 860
Trp Gly Asn Arg Phe Lys Lys Leu Ala Asp Met Tyr Gly Gly Gly Glu
865             870             875                         880
Asp Asp
```

FIG. 3
A
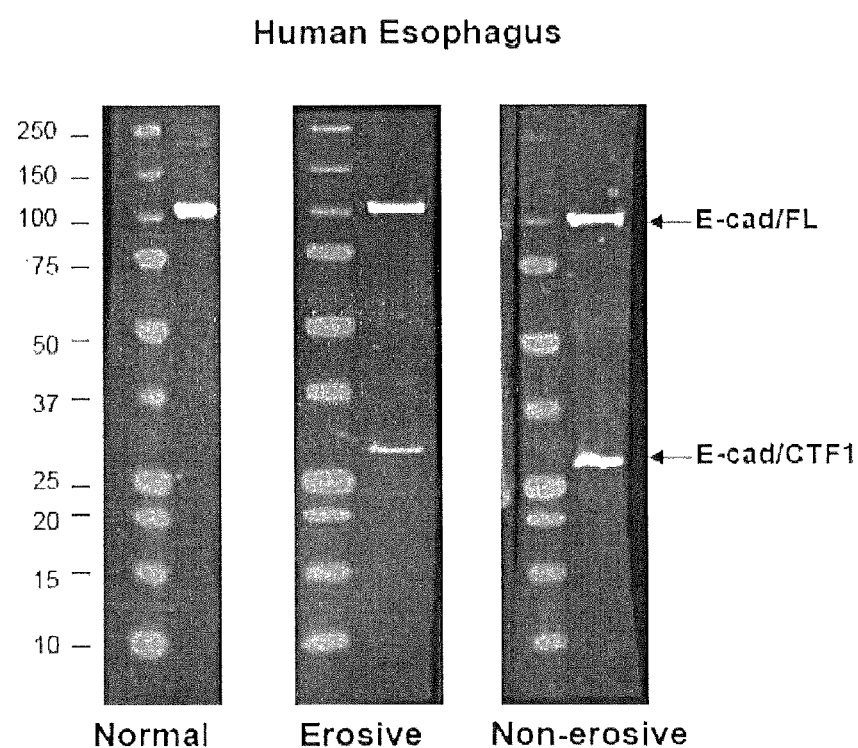
Human Esophagus
B
Mouse Embryos
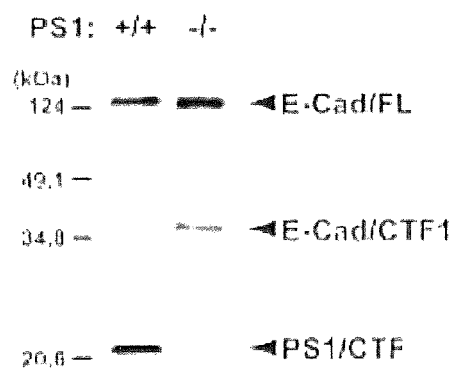

FIG. 4
A
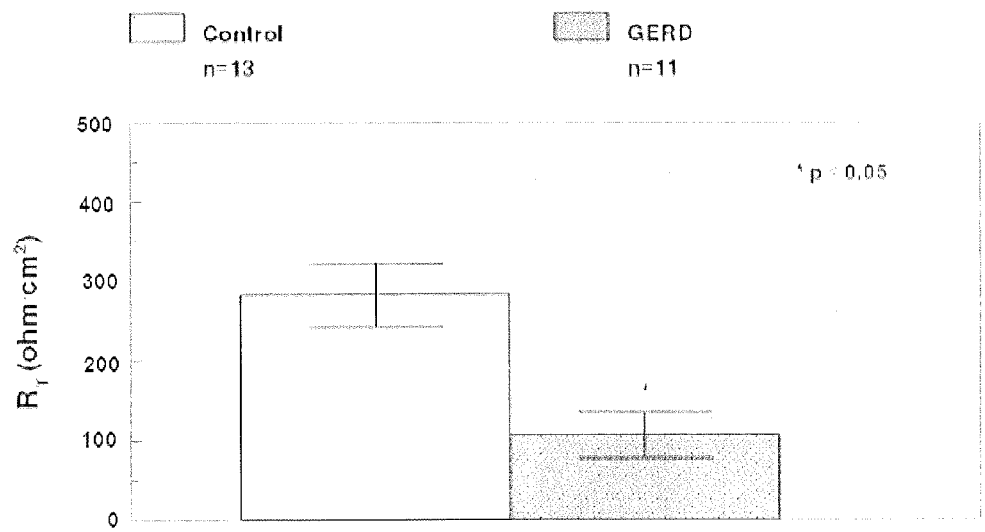
B
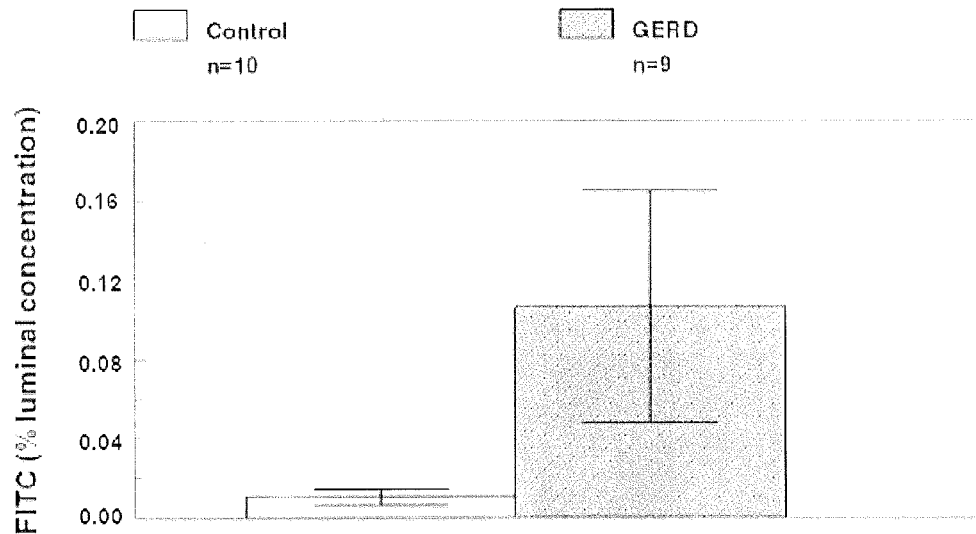

FIG. 9
A
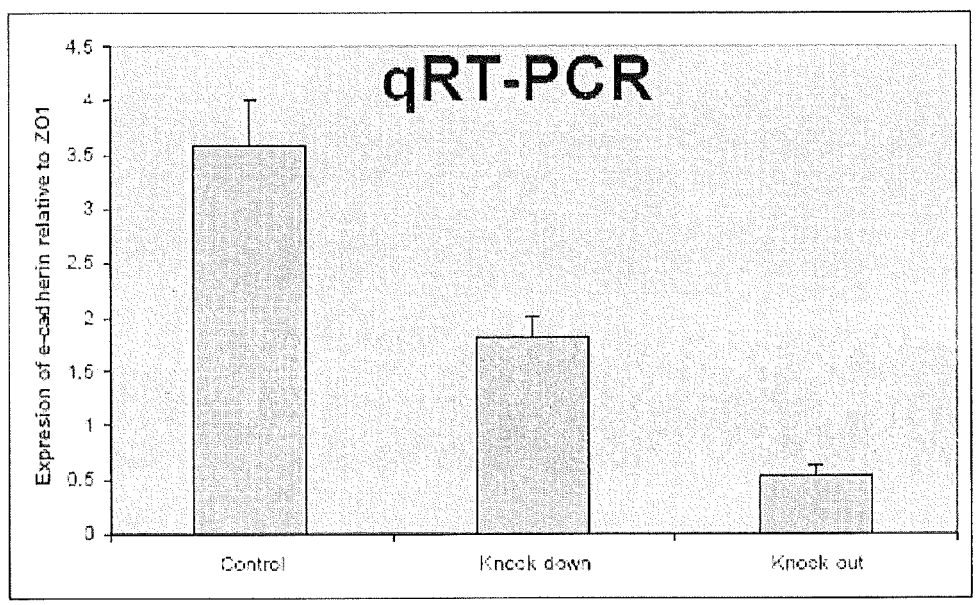
B
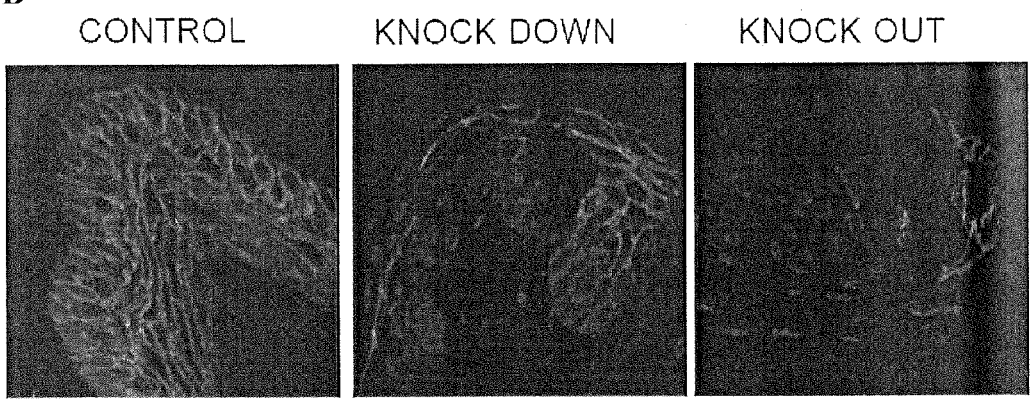

C

SEQUENCE LISTING

<160> NUMBER OF SEQ ID NOS: 1

<210> SEQ ID NO 1
<211> LENGTH: 882
<212> TYPE: PRT
<213> ORGANISM: Homo sapiens

<400> SEQUENCE: 1

```
Met Gly Pro Trp Ser Arg Ser Leu Ser Ala Leu Leu Leu Leu Leu Gln
1               5                  10                  15

Val Ser Ser Trp Leu Cys Gln Glu Pro Glu Pro Cys His Pro Gly Phe
            20                  25                  30

Asp Ala Glu Ser Tyr Thr Phe Thr Val Pro Arg Arg His Leu Glu Arg
        35                  40                  45
```

```
Gly Arg Val Leu Gly Arg Val Asn Phe Glu Asp Cys Thr Gly Arg Gln
 50                  55                  60

Arg Thr Ala Tyr Phe Ser Leu Asp Thr Arg Phe Lys Val Gly Thr Asp
 65                  70                  75                  80

Gly Val Ile Thr Val Lys Arg Pro Leu Arg Phe His Asn Pro Gln Ile
                 85                  90                  95

His Phe Leu Val Tyr Ala Trp Asp Ser Thr Tyr Arg Lys Phe Ser Thr
            100                 105                 110

Lys Val Thr Leu Asn Thr Val Gly His His His Arg Pro Pro His
        115                 120                 125

Gln Ala Ser Val Ser Gly Ile Gln Ala Glu Leu Leu Thr Phe Pro Asn
        130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
                165                 170                 175

Gln Ile Lys Ser Asn Lys Asp Lys Glu Gly Lys Val Phe Tyr Ser Ile
            180                 185                 190

Thr Gly Gln Gly Ala Asp Thr Pro Pro Val Gly Val Phe Ile Ile Glu
        195                 200                 205

Arg Glu Thr Gly Trp Leu Lys Val Thr Glu Pro Leu Asp Arg Glu Arg
        210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
                245                 250                 255

Asp Asn Lys Pro Glu Phe Thr Gln Glu Val Phe Lys Gly Ser Val Met
            260                 265                 270

Glu Gly Ala Leu Pro Gly Thr Ser Val Met Glu Val Thr Ala Thr Asp
        275                 280                 285

Ala Asp Asp Asp Val Asn Thr Tyr Asn Ala Ala Ile Ala Tyr Thr Ile
        290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
                325                 330                 335

Ser Phe Pro Thr Tyr Thr Leu Val Val Gln Ala Ala Asp Leu Gln Gly
            340                 345                 350

Glu Gly Leu Ser Thr Thr Ala Thr Ala Val Ile Thr Val Thr Asp Thr
        355                 360                 365

Asn Asp Asn Pro Pro Ile Phe Asn Pro Thr Thr Tyr Lys Gly Gln Val
        370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
                405                 410                 415

Asn Asp Asp Gly Gly Gln Phe Val Val Thr Thr Asn Pro Val Asn Asn
            420                 425                 430

Asp Gly Ile Leu Lys Thr Ala Lys Gly Leu Asp Phe Glu Ala Lys Gln
        435                 440                 445

Gln Tyr Ile Leu His Val Ala Val Thr Asn Val Val Pro Phe Glu Val
        450                 455                 460

Ser Leu Thr Thr Ser Thr Ala Thr Val Thr Val Asp Val Leu Asp Val
```

-continued

```
              465                 470                 475                 480
Asn Glu Ala Pro Ile Phe Val Pro Pro Glu Lys Arg Val Glu Val Ser
                    485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
        515                 520                 525
Thr Ala Asn Trp Leu Glu Ile Asn Pro Asp Thr Gly Ala Ile Ser Thr
    530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
                565                 570                 575
Gly Thr Gly Thr Leu Leu Leu Ile Leu Ser Asp Val Asn Asp Asn Ala
            580                 585                 590
Pro Ile Pro Glu Pro Arg Thr Ile Phe Phe Cys Glu Arg Asn Pro Lys
        595                 600                 605
Pro Gln Val Ile Asn Ile Ile Asp Ala Asp Leu Pro Pro Asn Thr Ser
    610                 615                 620
Pro Phe Thr Ala Glu Leu Thr His Gly Ala Ser Ala Asn Trp Thr Ile
625                 630                 635                 640
Gln Tyr Asn Asp Pro Thr Gln Glu Ser Ile Ile Leu Lys Pro Lys Met
                645                 650                 655
Ala Leu Glu Val Gly Asp Tyr Lys Ile Asn Leu Lys Leu Met Asp Asn
            660                 665                 670
Gln Asn Lys Asp Gln Val Thr Thr Leu Glu Val Ser Val Cys Asp Cys
        675                 680                 685
Glu Gly Ala Ala Gly Val Cys Arg Lys Ala Gln Pro Val Glu Ala Gly
    690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Phe Leu Arg Arg Arg Ala Val
                725                 730                 735
Val Lys Glu Pro Leu Leu Pro Pro Glu Asp Asp Thr Arg Asp Asn Val
            740                 745                 750
Tyr Tyr Tyr Asp Glu Glu Gly Gly Glu Glu Asp Gln Asp Phe Asp
        755                 760                 765
Leu Ser Gln Leu His Arg Gly Leu Asp Ala Arg Pro Glu Val Thr Arg
    770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
                805                 810                 815
Ala Ala Asp Thr Asp Pro Thr Ala Pro Pro Tyr Asp Ser Leu Leu Val
            820                 825                 830
Phe Asp Tyr Glu Gly Ser Gly Ser Glu Ala Ala Ser Leu Ser Ser Leu
        835                 840                 845
Asn Ser Ser Glu Ser Asp Lys Asp Gln Asp Tyr Asp Tyr Leu Asn Glu
    850                 855                 860
Trp Gly Asn Arg Phe Lys Lys Leu Ala Asp Met Tyr Gly Gly Gly Glu
865                 870                 875                 880

Asp Asp
```

E-CADHERIN AS A BIOMARKER OF GASTROESOPHAGEAL REFLUX DISEASE

STATEMENT OF PRIORITY

This application is a continuation-in-part application of International Application No. PCT/US2010/036634 filed May 28, 2010, which claims the benefit of priority from U.S. Provisional Application Ser. No. 61/182,400; filed May 29, 2009, which applications are incorporated herein by reference in their entireties.

GOVERNMENT SUPPORT

The present invention was made with government support under grant number DK 036013 awarded by the National Institutes of Health. The U.S. Government has certain rights in this invention.

FIELD OF THE INVENTION

The present invention provides methods directed to screening for and diagnosing gastroesophageal reflux disease (GERD) using E-cadherin as a biomarker.

BACKGROUND OF THE INVENTION

The most common manifestation of gastroesophageal reflux disease (GERD) is the symptom of heartburn, a substernal burning discomfort, often worse after meals and on reclining and temporarily relieved by antacids. Based on estimates that 20% of adults, ~27 million people, have heartburn at least weekly, GERD is one of the most common conditions in Americans. It is also costly because of procedures used in diagnosis and in prescriptions for proton pump inhibitors (PPI) used in treatment, the latter now costing $13.9 billion dollars per year. Moreover, heartburn occurs at night as well as day (1), and so interferes with sleep and work, impairing both productivity and quality of life. Though rarely a cause of death, ⅓rd of GERD subjects have on esophagogastroduodenoscopy (EGD) erosive esophagitis, and this may progress to strictures or Barrett's esophagus, the latter a risk factor for esophageal adenocarcinoma. The remaining two-thirds with GERD have heartburn but a negative EGD and so are said to have nonerosive reflux disease (NERD) (2). For confirmation of NERD, many patients undergo 24 hour esophageal pH monitoring, a test performed using wire-based or wireless devices; however, both are time consuming, costly, oftentimes unpleasant and imperfect, with up to 50% of those with NERD having normal esophageal pH monitoring (3). This leaves approximately 9 million adults with a diagnosis of NERD based solely on history of heartburn or history of heartburn coupled with response to 'empiric' PPI therapy. Heartburn, however, is not specific for GERD, resulting in PPI therapy being over-prescribed and, because symptom response is often equivocal, continued for long periods even when ineffective. This situation could be avoided were there readily available biomarkers of GERD that enabled the clinician to diagnose GERD or more specifically NERD that is responsive to PPI therapy.

Accordingly, the present invention addresses the previous shortcomings of the art by providing methods for diagnosis of GERD through the detection of the biomarkers, E-cadherin N-terminal fragments and/or E-cadherin C-terminal fragments.

SUMMARY OF THE INVENTION

Accordingly, a first aspect of the present invention provides a method of identifying a subject as having gastroesophageal reflux disease (GERD) comprising detecting the presence or absence of an increase in the amount of E-cadherin N-terminal fragments (NTF) in a sample from said subject, wherein an increase in the amount of E-cadherin NTF in said sample identifies the subject as having GERD.

In an additional aspect, the present invention provides a method of identifying a subject as having gastroesophageal reflux disease (GERD) comprising detecting the presence or absence of E-cadherin C-terminal fragments (CTF) in a sample from said subject, wherein the presence of E-cadherin CTF in said sample identifies the subject as having GERD.

In some aspects, the present invention provides a method of identifying a subject having an increased likelihood of a rapid relapse of GERD after reducing the dosage of or terminating proton pump inhibitor therapy comprising detecting the presence or absence of an increase in the amount of E-cadherin N-terminal fragment (NTF) in a sample from said subject, wherein the presence of an increase in the amount of E-cadherin NTF in said sample identifies the subject as having an increased likelihood of a rapid relapse of GERD after reducing the dosage of or terminating proton pump inhibitor therapy.

Further provided herein is a method of identifying a subject as having an increased likelihood of a rapid relapse of GERD after reducing dosage of or terminating proton pump inhibitor therapy comprising detecting the presence or absence of E-cadherin C-terminal fragments (CTF) in a sample from said subject, wherein the presence of E-cadherin CTF in said esophageal sample identifies the subject as having an increased likelihood of a rapid relapse of GERD after reducing dosage of or terminating proton pump inhibitor therapy.

An additional aspect of the invention provides a method of monitoring the healing of reflux esophagitis (i.e., erosive and/or nonerosive esophagitis) in a subject comprising: detecting the amount of E-cadherin N-terminal fragments (NTF) in a first sample from a subject prior to beginning treatment for reflux esophagitis; detecting the amount of E-cadherin NTF in a second sample from said subject at a time point after treatment for reflux esophagitis has begun; and comparing the amount of E-cadherin NTF in said first and second samples, whereby a decrease in the amount of E-cadherin NTF between the first sample and the second sample indicates the healing of reflux esophagitis in said subject. Such monitoring can be done in conjunction with or without the use of esophagogastroduodenoscopy and biopsy.

Other and further objects, features and advantages would be apparent and more readily understood by reading the following specification and by reference to the accompanying drawings forming a part thereof, or any examples of the embodiments of the invention given for the purpose of the disclosure.

BRIEF DESCRIPTION OF THE FIGURES

FIG. 1. E-cadherin amino acid sequence (human) (UniProtKB/Swiss-Prot P12830).

FIGS. 3A-B. Cleavage of E-cadherin in human esophagus (A) and mouse embryos (B). (A) E cadherin is cleaved in GERD but not in healthy EE. (B) cleavage of E-cadherin in a mouse model results in a smaller CTF as a result of the activity of γ-secretase (Marambaud et al. (*EMBO J.* 2(8):1948 (2002)).

FIGS. 4A-B. (A) Basal transepithelial electrical resistance ($R_T$) and (B) mucosal-to-serosal fluorescein fluxes are shown for the esophageal epithelium (EE) from patients with GERD and from subjects with a healthy esophagus (controls). Values were obtained for EE by mounting endoscopic biopsies in mini-Ussing chambers while bathed by normal Ringer on both sides. The mean basal $R_T$ from GERD, n=11, is significantly lower than from controls, n=13 while mean fluorescein flux from GERD, n=9, is significantly higher than from controls, n=10. Values are means±standard error, $p<0.05$ vs controls.

DETAILED DESCRIPTION OF THE INVENTION

Figure 2:
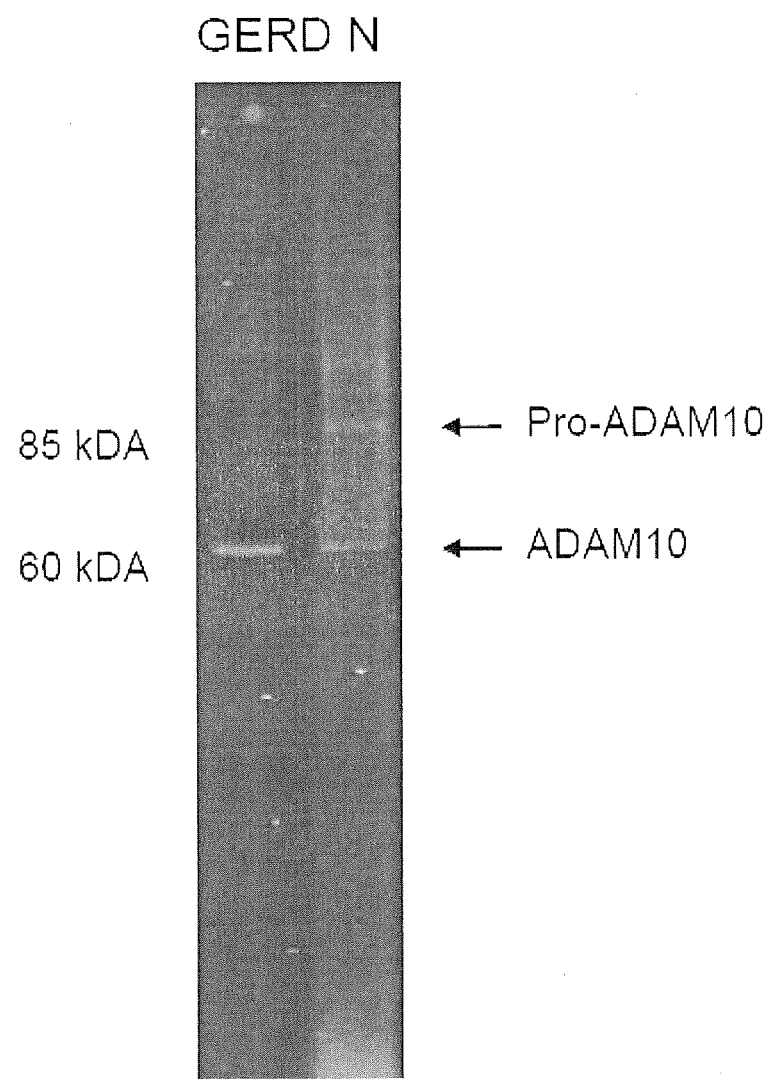
FIG. 2. Western blot of ADAM-10 is shown for esophageal epithelium (EE) from patients with GERD and from subjects with a healthy esophagus (controls). Ten micrograms of protein are loaded in each lane and immunodetection for ADAM-10 performed with a C-terminus antibody. Note that in control EE, there are two bands for ADAM-10, representing the 85 kDa intact molecule and a smaller 60 kD band representing the active form of the molecule. In the EE from GERD, only the smaller active form of ADAM-10 is identified.

This description is not intended to be a detailed catalog of all the different ways in which the invention may be implemented, or all the features that may be added to the instant invention. For example, features illustrated with respect to one embodiment may be incorporated into other embodiments, and features illustrated with respect to a particular embodiment may be deleted from that embodiment. In addition, numerous variations and additions to the various embodiments suggested herein will be apparent to those skilled in the art in light of the instant disclosure, which do not depart from the instant invention. Hence, the following descriptions are intended to illustrate some particular embodiments of the invention, and not to exhaustively specify all permutations, combinations and variations thereof.

The present inventors have discovered that contact of the esophageal epithelium with acid refluxates causes GERD by impairing junctional adhesion by E-cadherin, and that this impairment, initially reversible, becomes irreversible because of cleavage of E-cadherin's extracellular domain by activation of Adam-10. Moreover, cleavage of E-cadherin persists in GERD even when gastric acidity is controlled by proton pump inhibitors (PPIs) either because of proteolysis by trypsin and/or because of activation of Adam-10 by bile salts within refluxates of neutral pH. Additionally, since C-terminal fragments (CTFs) of E-cadherin are detectable in biological samples and increased quantities of N-terminal (NTFs) of (soluble) E-cadherin are detectable in biological samples, their utility as biomarkers for the diagnosis of GERD is useful in a number of well-defined clinical settings including, but not limited to, the detection of CTFs of E-cadherin and/or elevated quantities of NTFs and/or CTFs of E-cadherin for the diagnosis of GERD; the detection of CTFs and/or elevated quantities of NTFs and/or CTFs of E-cadherin in biological samples to distinguish between patients with heartburn, chest pain, dysphagia, cough, throat clearing, hoarseness and/or wheezing responsive to proton pump inhibitors (PPIs) and to distinguish between patients with heartburn, chest pain, dysphagia, cough, throat clearing, hoarseness and/or wheezing that are unresponsive to PPIs; the detection of CTFs and/or elevated quantities of NTFs and/or CTFs of E-cadherin in biological samples to distinguish between patients with esophagitis due to GERD and patients with esophagitis due to other causes; the detection of elevated quantities of NTFs and/or CTFs of E-cadherin and/or the detection of CTFs in biological samples to distinguish between patients with GERD who relapse rapidly after stopping PPIs and patients with GERD whose relapse is delayed after stopping PPIs; and the detection of NTFs of E-cadherin to monitor the healing of erosive and nonerosive esophagitis without the need for esophagogastroduodenoscopy or esophagogastroduodenoscopy with biopsy, respectively.

DEFINITIONS

As used herein, "a," "an" or "the" can mean one or more than one. For example, "a" cell can mean a single cell or a multiplicity of cells.

As used herein, "and/or" refers to and encompasses any and all possible combinations of one or more of the associated listed items, as well as the lack of combinations when interpreted in the alternative ("or").

Further, the term "about," as used herein when referring to a measurable value such as an amount or size of a compound or fragment, (e.g., size of E-cadherin N-terminal and C-terminal fragments) or agent, dose, time, temperature, and the like, is meant to encompass variations of ±20%, ±10%, ±5%, ±1%, ±0.5%, or even ±0.1% of the specified amount or size.

As used herein, the term "polypeptide" encompasses both peptides and proteins, unless indicated otherwise.

As used herein, an "isolated" polypeptide or polypeptide fragment means a polypeptide or polypeptide fragment separated or substantially free from at least some of the other components of the naturally occurring organism, for example, the cellular components or other polypeptides or nucleic acids commonly found associated with the polypeptide.

An "effective" amount as used herein is an amount of a compound or composition that is sufficient to achieve the intended effect, e.g., to treat and/or prevent a disorder in a subject. The effective amount will vary with the age, general condition of the subject, the severity of the condition being treated, the particular agent administered, the duration of the treatment, the nature of any concurrent treatment, the pharmaceutically acceptable carrier used, and like factors within the knowledge and expertise of those skilled in the art. As appropriate, an "effective amount" in any individual case can be determined by one of ordinary skill in the art by reference to the pertinent texts and literature and/or by using routine experimentation. (See, for example, Remington, *The Science And Practice of Pharmacy* (20th ed. 2000)).

When used in a therapeutic context, an "effective" amount is an amount sufficient to provide some improvement or benefit to the subject, e.g., an amount that provides some alleviation, mitigation or decrease in at least one clinical symptom, a delay or reduction in the progression of the disorder, and/or prevention or delay of the onset of the disorder. Those skilled in the art will appreciate that the therapeutic effects need not be complete or curative, as long as some benefit is provided to the subject.

By the term "treat," "treating" or "treatment of" (or grammatically equivalent terms) it is meant that the severity of the subject's condition is reduced or at least partially improved or ameliorated and/or that some alleviation, mitigation or decrease in at least one clinical symptom is achieved and/or there is a delay in the progression of the condition and/or prevention or delay of the onset of a disease or disorder. The term "treat," "treats," "treating," or "treatment of" and the like also include prophylactic treatment of the subject. As used herein, the term "prevent," "prevents," or "prevention" (and grammatical equivalents thereof) are not meant to imply complete abolition of disease and encompasses any type of prophylactic treatment that reduces the incidence of the condition, delays the onset and/or progression of the condition, and/or reduces the symptoms associated with the condition. Thus, unless the context indicates otherwise, the term "treat," "treating" or "treatment of" (or grammatically equivalent terms) refer to both prophylactic and therapeutic regimens.

By the term "responsive" is meant that a subject that is provided a particular treatment for a particular disease or disorder shows an improvement or reduction in symptoms related to that disease or disorder in response to that treatment. "Non-responsive" means that a subject that is provided a particular treatment for a particular disease or disorder fails to show an improvement or reduction in symptoms related to that disease or disorder in response to that treatment.

As used herein, the transitional phrase "consisting essentially of" means that the scope of a claim is to be interpreted to encompass the specified materials or steps recited in the claim and those that do not materially affect the basic and novel characteristic(s) of the claimed invention. Thus, the term "consisting essentially of" when used in a claim of this invention is not intended to be interpreted to be equivalent to "comprising."

The terms "increased risk" or "increased likelihood" as used herein defines the level of risk or the likelihood that a subject has of having GERD, having heartburn or other symptoms of GERD (e.g., chest pain, dysphagia, cough, throat clearing, hoarseness or wheezing) that are responsive to proton pump inhibitor (PPI) therapy, and/or having an increased likelihood of a rapid relapse of GERD after termination of PPI therapy as compared to a control subject that does not have GERD, does not have heartburn or other symptoms of GERD, and/or has a delayed relapse of GERD after termination of PPI therapy, respectively.

The terms "reduced risk," "reduced likelihood," "decreased risk," or "decreased likelihood" as used herein defines the level of risk or the likelihood that a subject has of having GERD, having heartburn or other symptoms of GERD (e.g., chest pain, dysphagia, cough, throat clearing, hoarseness or wheezing) that are responsive or nonresponsive to proton pump inhibitor (PPI) therapy, and/or having an reduced likelihood of a rapid relapse of GERD after termination of PPI therapy as compared to a control subject that does not have GERD, does not have heartburn or other symptoms of GERD, and/or has a delayed relapse of GERD after termination of PPI therapy, respectively.

A "change" in the level, amount, concentration, ratio and the like with respect to an E-cadherin fragment(s) can mean an increase or a decrease. As used herein the term "level" is intended broadly and can mean a qualitative amount, a quantitative amount (e.g., weight or moles), a semi-quantitative amount, a relative amount (e.g., weight % or mole % or as compared to a control), a concentration, and the like.

The present invention provides a method for diagnosing GERD, a condition commonly associated with the symptoms of heartburn, chest pain, dysphagia, cough, throat clearing, hoarseness and/or wheezing with or without esophageal erosions on endoscopy. The invention is based in part on the ability to detect active damage to stratified squamous epithelium, e.g. the esophageal epithelium (EE), by refluxed gastric contents through the detection of cleaved fragments of the protein, E-cadherin, in biological samples. The association of E-cadherin fragments with GERD is supported by comparative analysis of clinical samples from patients with GERD and patients with a healthy esophagus, and by evidence in animal models of GERD showing that cleavage of E-cadherin is found in association with a lesion known as 'dilated intercellular spaces' (DIS) on electron microscopy, the latter a known histopathologic feature of GERD in humans and one that correlates with heartburn. Since heartburn, erosions, 24 hour monitoring, histopathological changes such as dilated intercellular spaces and basal cell hyperplasia are not specific for the diagnosis of GERD, an objective biomarker would be highly valuable to aid in management decisions for suspected GERD in the clinical setting.

The esophagus is lined by a stratified squamous epithelium. This tissue is normally electrically 'tight' and so of very low permeability. One of the major reasons for its low permeability is that the intercellular junctions that guard permeation of molecules and ions between the cells is guarded by a tight junction which is supported by a junctional structure known as the zonula adherens. A major protein that forms the bridge across the intercellular space of the zonula adherens is E-cadherin, which is approximately 120 kD in size (FIG. 1).

This protein not only serves as the connecting link for the zonula adherens between neighboring cells but it is instrumental in maintaining the integrity of the tight junction which is located just above it on the luminal surface side of the junction and which is considered the critical regulator of ion and molecular permeability through the intercellular space. As is well known in the art, E-cadherin consists of a intramembrane domain, an intracellular (cytoplasmic) domain and an intercellular domain. (See, UniProtKB/Swiss-Prot P12830 (CADH1_HUMAN)). The intercellular domain of E-cadherin is comprised of five cadherin repeats. (See, FIG. 10)

In patients with GERD, the esophagus is attacked and damaged by gastric acid refluxed from the stomach and this leads to damage to the esophageal epithelium and to the symptom of heartburn. In these patients, the lesion observed on electron microscopy that correlates with heartburn is the known as 'dilated intercellular spaces'. The inventors have discerned that the cause for dilated intercellular spaces and the 'leakiness' of esophageal epithelium upon exposure to acid is the cleavage of E-cadherin by an acid-activated enzyme (Adam-10) within the tissue. Adam-10 is a metalloproteinase that cleaves extracellular E-cadherin at the cell membrane resulting in C-terminal fragments (CTF) (e.g., CTF1, approximately 38 kD; CTF2, approximately 33 kD; CTF3, approximately 29 kD) buried in the tissue (and extending into the intracellular (cytoplasmic) space), which can be detected in tissue samples (e.g., biopsies), and soluble N-terminal fragments (NTF) (approximately 85 kD in size) which are released into and detectable in biological fluids (e.g., blood, gastric juice, serum, tears, urine, and the like). In certain other species, such as rabbits, a C-terminal fragment is often detected that is 25 kD in size (CTF2) due to the presence of an enzyme (γ-secretase) that cleaves the C-terminal fragment further. For non-limiting examples of cleaved E-cadherin fragments see, UniProtKB/Swiss-Prot P12830—providing the cleavage sites of human E-cadherin for (1) metalloproteinase at amino acids 700-701 resulting in a fragment of about 38 kD; (2) γ-secretase at amino acids 731-732 resulting in a fragment of about 33 kD; and (3) caspase 3 at amino acids 750-751 resulting in a fragment of about 29 kD. (See also, Bussemakers et al. *Mol. Biol. Rep.* 17:123-128 (1993); Maretsky et al. *Dermatology J.* 128:1737-1747 (2008); Steinhusen et al. *J. Biol. Chem.* 276:4972-4980 (2001); Ito et al. *Oncogene* 18:7080-7090 (1999); and Marambaud *EMBO J.* 21:1948-1956 (2002)).) Both the C-terminal fragments and the N-terminal fragments are detectable using any antibody that is directed to a C-terminal or N-terminal E-cadherin fragment.

Moreover, evidence of cleavage of E-cadherin in samples (e.g., esophageal biopsies) from patients with GERD was detected, but not in samples (e.g., esophageal biopsies) for subjects with a healthy esophagus. Further, the part of the cleaved protein that is released in the process can be detected in increased quantities in biological samples of patients with GERD. Thus, the presence of E-cadherin fragments is correlated with the GERD disease condition and indicates that detection of cleaved fragments of E-cadherin in biological samples can serve as biomarkers for the diagnosis of GERD. For example, antibodies directed against E-cadherin C-terminal fragments (CTF) (e.g., Mab 4A2C7 (Zymed, Carlsbad, Calif.), and the like) or antibodies directed to the E-cadherin N-terminal fragments (NTF) (e.g., Mab HECD-1 (Zymed, Carlsbad, Calif.), and the like) can be used to detect cleaved fragments of E-cadherin. Such biomarkers have considerable value in the clinical setting because of sensitivity and/or specificity of intraesophageal pH and impedance monitoring and lack of specificity of the endoscopic signs (erosions) and symptoms (heartburn) of GERD, but which are the current methods of diagnosis:

As noted above, any antibody directed to an E-cadherin N-terminal fragment can be used in the methods of the present invention to detect the E-cadherin NTFs of the present invention. Likewise, any antibody directed to an E-cadherin C-terminal fragment can be used in the methods of the present invention to detect the E-cadherin CTFs, Further, any size E-cadherin CTF or E-cadherin NTF that is sufficient for an antibody to attach to can be used in the methods of the present invention (i.e., any E-cadherin fragment having an epitope and the C-terminus or the N-terminus of E-cadherin). Thus, an E-cadherin CTF of the present invention can be about 38 kD to about 1 kD in size. Thus in some embodiments, E-cadherin CTF is about 38 kD, about 37 kD, about 36 kD, about 35 kD, about 34 kD, about 33 kD, about 32 kD, about 31 kD, about 30 kD, about 29 kD, about 28 kD, about 27 kD, about 26 kD, about 25 kD, about 24 kD, about 23 kD, about 22 kD, about 21 kD, about 20 kD, about 19 kD, about 18 kD, about 17 kD, about 16 kD, about 15 kD, about 14 kD, about 13 kD, about 12 kD, about 11 kD, about 10 kD, about 9 kD, about 8 kD, about 7 kD, about 6 kD, about 5 kD, about 4 kD, about 3 kD, about 2 kD, about 1 kD, or any combination thereof.

An E-cadherin NTF of the present invention includes any size fragment of E-cadherin that includes the N-terminal end of the E-cadherin protein and at least one epitope. Thus, an E-cadherin NTF can be a size in a range of about 85 kD to about 1 kD. In other embodiments, an E-cadherin NTF is about 85 kD, about 84 kD, about 83 kD, about 82 kD, about 81 kD about 80 kD, about 79 kD, about 78 kD, about 77 kD, about 76 kD, about 75 kD, about 74 kD, about 73 kD, about 72 kD, about 71 kD, about 70 kD, about 69 kD, about 68 kD, about 67 kD, about 66 kD, about 65 kD, about 64 kD, about 63 kD, about 62 kD, about 61 kD, about 60 kD, about 59 kD, about 58 kD, about 57 kD, about 56 kD, about 55 kD, about 54 kD, about 53 kD, about 52 kD, about 51 kD, about 50 kD, about 49 kD, about 48 kD, about 47 kD, about 46 kD, about 45 kD, about 44 kD, about 43 kD, about 42 kD, about 41 kD, about 40 kD, about 39 kD, about 38 kD, about 37 kD, about 36 kD, about 35 kD, about 34 kD, about 331W, about 32 kD, about 31 kD, about 30 kD, about 29 kD, about 28 kD, about 27 kD, about 26 kD, about 25 kD, about 24 kD, about 23 kD, about 22 kD, about 21 kD, about 20 kD, about 191W, about 18 kD, about 17 kD, about 16 kD, about 15 kD, about 14 kD, about 13 kD, about 12 kD, about 11 kD, about 10 kD, about 9 kD, about 8 kD, about 71W, about 6 kD, about 5 kD, about 4 kD, about 3 kD, about 2 k, about 1 kD, or any combination thereof.

The utility of such biomarkers includes but is not limited to: a) distinguishing between patients with heartburn (and/or other symptoms of GERD such as chest pain, dysphagia, cough, throat clearing, hoarseness and/or wheezing) responsive to proton pump inhibitors (PPIs) and patients with heartburn, chest pain, dysphagia, cough, throat clearing, hoarseness and/or wheezing that is unresponsive to PPIs, (b) distinguishing between patients with esophagitis due to GERD and patients with esophagitis due to other causes, (c) distinguishing between patients with GERD who relapse rapidly after ending PPIs and patients with GERD whose relapse is delayed after stopping PPIs (a rapid relapse is defined as being a relapse that occurs at or within 6 months of ending PPI therapy, whereas a delayed relapse is defined as a relapse that occurs after 6 months subsequent to ending PPI therapy), d) distinguishing between patients presenting (e.g., in the ER) with acute chest pain from GERD and those presenting with acute chest pain from conditions other than GERD (e.g., cardiac event) and e) monitor the healing of erosive and non-erosive forms of esophagitis of GERD without the need for esophagogastroduodenoscopy or esophagogastroduodenoscopy and biopsy, respectively.

Thus, the present invention discloses methods of diagnosing and identifying subjects having GERD, identifying subjects having heartburn, chest pain, dysphagia, cough, throat clearing, hoarseness and/or wheezing that is responsive to PPI therapy, and/or identifying subjects having an increased likelihood of a rapid relapse of GERD after ending PPI therapy. In addition, the present invention provides methods for monitoring the healing of erosive and non-erosive esophagitis of GERD without the need for esophagogastroduodenoscopy or esophagogastroduodenoscopy and biopsy, respectively.

In some embodiments, a subject of this invention can have a diagnosis of GERD, and in other embodiments, a subject of this invention does not have a diagnosis of GERD. A subject of this invention can also be a subject having symptoms of GERD but without a diagnosis of GERD.

Accordingly, a first aspect of the present invention provides a method of identifying a subject as having gastroesophageal reflux disease (GERD) comprising detecting the presence or absence of an increase in the amount of E-cadherin N-terminal fragments (NTF) in a sample (e.g., blood, urine, tears, saliva, gastric juices, and the like) from said subject, wherein an increase in the amount of E-cadherin NTF in said sample identifies the subject as having GERD.

In some embodiments, the presence or absence of an increase in the amount of E-cadherin NTF in the sample (e.g., blood, urine, tears, saliva, gastric juices, and the like) of a subject is compared to the level of E-cadherin NTF in a sample (e.g., blood, urine, tears, saliva, gastric juices, and the like) from a control subject not having GERD. The level of E-cadherin NTF in a sample from a control subject not having GERD can be a predetermined amount. Thus, the presence or absence of an increase in the amount of E-cadherin NTF in the sample of a subject can be compared to a predetermined amount of E-cadherin NTF in a sample from a control subject not having GERD, wherein the presence of an increase in the amount of E-cadherin NTF identifies a subject as having GERD.

A second aspect of the invention provides a method of identifying a subject as having GERD comprising detecting the presence or absence of E-cadherin C-terminal fragments (CTF) in a sample (e.g., stratified squamous epithelial tissue) from said subject, wherein the presence of E-cadherin CTF in said sample identifies the subject as having GERD.

In some embodiments, the presence or absence E-cadherin CTF in a sample (e.g., stratified squamous epithelial tissue) from a subject is compared to the level of E-cadherin CTF in a sample (e.g., stratified squamous epithelial tissue) from a control subject not having GERD. The level of E-cadherin CTF in said sample from a control subject not having GERD can be a predetermined amount. In some embodiments, said predetermined amount can be zero. Thus, the presence or absence E-cadherin CTF in the sample from a subject can be compared to a predetermined amount of E-cadherin CTF in the sample from a control subject not having GERD, wherein the presence of E-cadherin CTF in the sample from a subject identifies the subject as having GERD.

Thus, the presence of E-cadherin CTF in a sample from a subject as compared to the absence of E-cadherin CTF in a sample from a control subject not having GERD identifies the subject as having GERD.

A third aspect of the present invention provides a method of identifying a subject as having GERD comprising detecting the presence or absence of an increase in the amount of E-cadherin CTF in a sample from said subject, wherein an increase in the amount of E-cadherin CTF in said sample identifies the subject as having GERD.

In embodiments, the presence or absence of an increase in the amount of E-cadherin CTF in a sample from a subject is compared to the level or amount of E-cadherin CTF in a sample from a control subject not having GERD. The level of E-cadherin CTF in a sample from a control subject not having GERD can be a predetermined amount. Thus, the presence or absence of an increase in the amount of E-cadherin CTF in a sample from a subject can be compared to a predetermined amount of E-cadherin CTF in a sample from a control subject not having GERD, wherein the presence of an increase in the amount of E-cadherin CTF in the sample from the subject identifies the subject as having GERD.

A "subject" of this invention includes any animal susceptible to GERD. Such a subject is generally a mammalian subject, including but not limited to human, primate, dog, cat, pig, rabbit, rat, mouse, guinea pig, goat, bovine, horse, and the like. Thus, in some embodiments, a subject can be any domestic, commercially or clinically valuable animal including an animal model of GERD (e.g., rabbit, rat, pig, cat). Subjects may be male or female and may be any age including neonate, infant, juvenile, adolescent, adult, and geriatric subjects. In particular embodiments, the subject is a human. A human subject of this invention can be of any age, gender, race or ethnic group (e.g., Caucasian (white), Asian, African, black, African American, African European, Hispanic, Mideastern, etc.).

A sample of this invention can be any biological sample from a subject containing proteins, polypeptides, and fragments thereof, as would be well known to one of ordinary skill in the art. Nonlimiting examples of a biological sample of this invention include a cell, a body fluid (e.g., urine, tears, blood, saliva, gastric juice, bile, etc.), a tissue, a washing, a swabbing, etc., as would be well known in the art. In some embodiments of the present invention, the sample includes, but is not limited to, gastric juice, blood and body fluids derived from blood (e.g., urine, tears, and saliva). In particular embodiments, a sample of this invention is a blood sample. A blood sample as used herein includes but is not limited to plasma, serum and/or fractions, and/or any combination thereof. Thus, in some embodiments of the present invention, E-cadherin NTFs are detected in gastric juice, blood, tears, urine, saliva, and any combination thereof. Thus, in some embodiments of the invention, E-cadherin NTFs are detected in gastric juice. In other embodiments, E-cadherin NTFs are detected in tears. In still other embodiments, E-cadherin NTFs are detected in saliva. In further embodiments of the invention, E-cadherin NTFs are detected in urine.

In additional embodiments, a sample of this invention is a tissue sample. As used herein, a tissue sample includes, but is not limited to, a stratified squamous epithelial tissue sample, which is accessible to or can be contacted with the reflux gastric acid. Thus, in some embodiments, stratified squamous epithelial tissue sample includes, but is not limited to, esophagus, nasopharynx (e.g., nasopharyngeal epithelium), oropharynx (e.g., buccal mucosa, tongue, soft and hard palate), larynx, and any combination thereof. In further embodiments of the invention, a tissue sample includes, but is not limited to, a tissue sample of the rumen and forestomach. In some embodiments of the invention, a tissue sample is a biopsy (e.g, an esophageal tissue biopsy, a nasopharynx tissue biopsy, an oropharynx tissue biopsy, a larynx tissue biopsy, and any combination thereof). Thus, in some embodiments of the invention, E-cadherin CTFs are detected in a stratified squamous epithelial tissue sample from a subject. In further embodiments, E-cadherin CTFs are detected in an esophageal tissue biopsy, a nasopharynx tissue biopsy, an oropharynx tissue biopsy, a larynx tissue biopsy, and/or any combination thereof.

The step of collecting a sample can be carried out either directly or indirectly by any suitable technique. For example, a blood sample from a subject can be carried out by phlebotomy, finger stick, or any other suitable technique, with the blood sample processed further to provide a serum sample or other suitable blood fraction. In other embodiments of the present invention, a sample is collected in a biopsy.

The detection of E-cadherin fragments of this invention can be carried out according to various protocols standard in the art and as described herein for analyzing biological samples and polypeptides and fragments thereof (e.g., E-cadherin fragments) in such samples. For example, polypeptides and fragments thereof can be obtained from any suitable sample from the subject that will contain such polypeptides and fragments thereof. Detecting or determining the level of a polypeptide or polypeptide fragment of the invention can be carried out by any means known in the art and as described herein, including but not limited to, flow cytometry, affinity purification, immunocytochemistry, Western blots, immunoblots, immunoprecipitation, immunohistochemistry, immunofluorescence, enzyme-linked immunosorbant assays (ELISA), and radioimmunoassay, densitometry, column chromatography, and any combination thereof. Thus, for example, an immunoblot or Western blot (W-blot) can be prepared using the biological samples obtained from the subjects and then the fragments of E-cadherin can be detected using antibodies (e.g., monoclonal antibody 4A2C7 to E-cadherin C-terminal fragments; Zymed, Carlsbad, Calif.) and/or monoclonal antibody HECD-1 to E-cadherin N-terminal fragments; Zymed, Carlsbad, Calif.). Alternatively, the fragments of E-cadherin can be detected using ELISA or any other suitable method.

Antibodies that can be used with the present invention include any antibody capable of detecting E-cadherin, including polyclonal and/or monoclonal antibodies. Any epitope on the intracellular and/or the extracellular domains of E-cadherin can be used in the present invention for the detection of the E-cadherin NTF and CTF fragments, Many antibodies directed to E-cadherin are known in the art and are commercially available. Thus, examples of E-cadherin directed antibodies include, but are not limited to, HECD-1, 4A2C7, 67A4, MB2, Sec21, M168, SPM471, 5H9, EP700Y, EP913 (2)Y, DECMA-1, 6F9, 2F11, 3C12, 4D11, 6A7, 1C10, 1F12, 9F2, 1G5, Sec11, SHE78-7, SPM381, SPM471, and the like. Further, antibodies of the present invention include, but are not limited to, those listed at Biocompare.com.

As is well-known in the art, methods of antibody detection involve contacting the antigen (e.g., E-cadherin fragment(s)) with the antibody specific for that antigen in order to transform the antigen into an antigen-antibody complex that can then be detected by various art-known means as described above. Such methods of detection can be carried out automatically or partially automatically in a machine or apparatus designed to perform such assays, e.g., using computer-assisted methods. The results of the assays can be stored in a computer database and analyzed to produce diagnostic results. In some embodiments, the diagnostic data can be analyzed, e.g., by comparing intra-patient result's over time or before and after treatment or comparing inter-patient results to determine baseline and/or abnormal values in a population.

The detection of E-cadherin fragments (CTF and/or NTF) can be based on quantitative, semi-quantitative and/or qualitative analysis. Thus, as used herein the detection of the presence or absence of E-cadherin fragments can be based on quantitative, semi-quantitative and/or qualitative methods. As an example, qualitative methods can be used to detect the presence or absence of E-cadherin fragment(s) in a biological sample. Semi-quantitative methods can be used to determine a level of E-cadherin fragments above a threshold value without assigning an absolute or relative numerical value. Quantitative methods can be used to determine a relative or absolute amount of E-cadherin fragments in the biological sample.

In semi-quantitative methods, a threshold or cutoff value can be determined by any means known in the art, and is optionally a predetermined amount. In particular embodiments, the threshold value is predetermined in the sense that it is fixed, for example, based on previous experience with the assay and/or a population of subjects that have, for example, GERD. Alternatively, the term "predetermined amount" or "predetermined standard" can also indicate that the method of arriving at the threshold is predetermined or fixed even if the particular value varies among assays or may even be determined for every assay run.

The E-cadherin fragment biomarkers of this invention can be correlated with (i.e., identified to be statistically associated with) GERD as described herein according to methods well known in the art and as disclosed in the Examples provided herein for statistically correlating the E-cadherin fragments as markers with various phenotypic traits, including disease states and pathological conditions (e.g., GERD) as well as determining levels of risk or likelihood associated with developing or having a particular phenotype, such as a disease, disorder or pathological condition. In general, identifying such a correlation involves conducting analyses that establish a statistically significant association and/or a statistically significant correlation between the presence of a marker (e.g., E-cadherin fragments) and the phenotypic trait in a population of subjects and controls. An analysis that identifies a statistical association (e.g., a significant association) between the marker or combination of markers and the phenotype establishes a correlation between the presence of the marker or combination of markers in a population of subjects and the particular phenotype being analyzed. A level of risk or likelihood (e.g., increased or decreased) can then be determined for an individual on the basis of such population-based analyses.

In some embodiments, the methods of correlating the markers of the present invention with particular treatment regimens can be carried out using a computer database. Thus, in some embodiments, the present invention provides a computer-assisted method of identifying a proposed therapy and/or treatment for GERD as an effective and/or appropriate therapy and/or treatment for a subject that has GERD, comprising the steps of: (a) storing a database of biological data for a plurality of subjects, the biological data that is being stored including for each of said plurality of subjects: (i) therapy and/or treatment type, (ii) the amount or level of E-cadherin fragments (CTF and/or NTF), and (iii) at least one disease progression measure and/or symptom for GERD from which treatment and/or therapy efficacy can be determined; and then (b) querying the database to determine the dependence on said E-cadherin fragment(s) of the effectiveness of a treatment and/or therapy type in treating and/or managing GERD, thereby identifying a proposed treatment and/or therapy as an effective and/or appropriate treatment and/or therapy for a subject with GERD.

In one embodiment, treatment information for a subject is entered into the database (through any suitable means such as a window or text interface), marker information for that subject is entered into the database, and disease progression responsiveness to treatment information is entered into the database. These steps are then repeated until the desired number of subjects has been entered into the database. The database can then be queried to determine whether a particular treatment is effective for subjects carrying a particular marker or combination of markers, not effective for subjects carrying a particular marker or combination of markers, etc. Such querying can be carried out prospectively or retrospectively on the database by any suitable means, but is generally done by statistical analysis in accordance with known techniques.

A further aspect of the present invention provides a method of identifying a subject as having heartburn, chest pain, dysphagia, cough, throat clearing, hoarseness and/or wheezing that is responsive to proton pump inhibitor therapy comprising detecting the presence or absence of an increase in the amount of E-cadherin N-terminal fragments (NFT) in a sample (e.g., gastric juice, blood, urine, tears, saliva, and the like) from said subject, wherein the presence of an increase in the amount of E-cadherin NTF in said sample identifies the subject as having heartburn, chest pain, dysphagia, cough, throat clearing, hoarseness and/or wheezing that is responsive to proton pump inhibitor therapy. Alternatively, the absence of an increase in the amount of E-cadherin NTF in said sample identifies the subject as having heartburn, chest pain, dysphagia, cough, throat clearing, hoarseness and/or wheezing that is non-responsive to proton pump inhibitor therapy.

The presence or absence of an increase in the amount of E-cadherin NTF in the sample of a subject is compared to the level of E-cadherin NTF in a sample from a control subject not having heartburn, chest pain, dysphagia, cough, throat clearing, hoarseness and/or wheezing. The level of E-cadherin NTF in a sample from a control subject not having heartburn, chest pain, dysphagia, cough, throat clearing, hoarseness and/or wheezing can be a predetermined amount. Thus, the presence or absence of an increase in the amount of E-cadherin NTF in a sample from a subject can be compared to a predetermined amount of E-cadherin NTF in a sample from a control subject not having heartburn, chest pain, dysphagia, cough, throat clearing, hoarseness and/or wheezing, wherein the presence of an increase in the amount of E-cadherin NTF identifies a subject as having heartburn that is responsive to proton pump inhibitor therapy and wherein the absence of an increase in the amount of E-cadherin NTF in said sample identifies the subject as having heartburn that is non-responsive to proton pump inhibitor therapy.

The present invention further provides a method of identifying a subject as having heartburn, chest pain, dysphagia, cough, throat clearing, hoarseness and/or wheezing that is responsive to proton pump inhibitor therapy comprising detecting the presence or absence of E-cadherin CTF in a sample (e.g., stratified squamous epithelial tissue) from said subject, wherein the presence of E-cadherin CTF in said sample identifies the subject as having heartburn, chest pain, dysphagia, cough, throat clearing, hoarseness and/or wheezing that is responsive to proton pump inhibitor therapy. Alternatively, the absence of E-cadherin CTF in said sample identifies the subject as having heartburn, chest pain, dysphagia, cough, throat clearing, hoarseness and/or wheezing that is nonresponsive to proton pump inhibitor therapy.

In other aspects the invention, the presence or absence of E-cadherin CTF in a sample (e.g., stratified squamous epithelial tissue) from a subject is compared to the level of E-cadherin CTF in a sample (e.g., stratified squamous epithelial tissue) from a control subject not having heartburn, chest pain, dysphagia, cough, throat clearing, hoarseness and/or wheezing. The level of E-cadherin CTF in a sample from a control subject not having heartburn, chest pain, dysphagia, cough, throat clearing, hoarseness and/or wheezing can be a predetermined amount. In some embodiments, said predetermined amount can be zero. Thus, the presence or absence E-cadherin CTF in a sample from a subject can be compared to a predetermined amount of E-cadherin CTF in a sample from a control subject not having heartburn, chest pain, dysphagia, cough, throat clearing, hoarseness and/or wheezing, wherein the presence E-cadherin CTF in the sample from a subject identifies the subject as having heartburn, chest pain, dysphagia, cough, throat clearing, hoarseness and/or wheezing that is responsive to proton pump inhibitor therapy and wherein the absence of E-cadherin CTF in said sample identifies the subject as having heartburn, chest pain, dysphagia, cough, throat clearing, hoarseness and/or wheezing that is nonresponsive to proton pump inhibitor therapy.

An additional aspect of the present invention provides a method of identifying a subject as having heartburn, chest pain, dysphagia, cough, throat clearing, hoarseness and/or wheezing that is responsive to proton pump inhibitor therapy comprising detecting the presence or absence of an increase in the amount of E-cadherin CTF in a sample (e.g., stratified squamous epithelial tissue) from said subject, wherein the presence of an increase in the amount of E-cadherin CTF in said sample identifies the subject as having heartburn, chest pain, dysphagia, cough, throat clearing, hoarseness and/or wheezing that is responsive to proton pump inhibitor therapy and wherein the absence of an increase in the amount of E-cadherin CTF in said sample identifies the subject as having heartburn, chest pain, dysphagia, cough, throat clearing, hoarseness and/or wheezing that is nonresponsive to proton pump inhibitor therapy.

In further embodiments, the presence or absence of an increase in the amount of E-cadherin CTF in a sample (e.g., stratified squamous epithelial tissue) from a subject is compared to the level or amount of E-cadherin CTF in a sample (e.g., stratified squamous epithelial tissue) from a control subject not having heartburn, chest pain, dysphagia, cough, throat clearing, hoarseness and/or wheezing. The level of E-cadherin CTF in a sample from a control subject not having heartburn, chest pain, dysphagia, cough, throat clearing, hoarseness and/or wheezing can be a predetermined amount. Thus, the presence or absence of an increase in the amount of E-cadherin CTF in a sample from a subject can be compared to a predetermined amount of E-cadherin CTF in a sample from a control subject not having heartburn, chest pain, dysphagia, cough, throat clearing, hoarseness and/or wheezing, wherein the presence of an increase in the amount of E-cadherin CTF in the sample from a subject identifies the subject as having heartburn, chest pain, dysphagia, cough, throat clearing, hoarseness and/or wheezing that is responsive to proton pump inhibitor therapy and wherein the absence of an increase in the amount of E-cadherin CTF in said sample identifies the subject as having heartburn, chest pain, dysphagia, cough, throat clearing, hoarseness and/or wheezing that is nonresponsive to proton pump inhibitor therapy.

The present invention additionally provides a method of identifying a subject as having an increased likelihood of (at risk for) a rapid relapse of GERD after reducing the dosage of or terminating or ending PPI therapy comprising detecting the presence or absence of an increase in the amount of E-cadherin NTF in a sample (e.g., gastric juice, blood, urine, tears, saliva, and the like) from said subject, wherein the presence of an increase in the amount of E-cadherin NTF in said sample identifies the subject as having an increased likelihood of a rapid relapse of GERD after reducing the dosage of or terminating proton pump inhibitor therapy. As used herein, a rapid relapse is a relapse that occurs at or within 6 months after reducing the dosage of or ending PPI therapy, whereas a delayed relapse is a relapse that occurs after 6 months following reducing the dosage of or ending PPI therapy.

Thus, in embodiments, the presence or absence of an increase in the amount of E-cadherin NTF in the sample (e.g., gastric juice, blood, urine, tears, saliva, and the like) from a subject is compared to the level of E-cadherin NTF in a sample (e.g., gastric juice, blood, urine, tears, saliva, and the like) from a control subject not having heartburn or other symptoms of GERD (e.g., chest pain, dysphagia, cough, throat clearing, hoarseness and/or wheezing). The level of E-cadherin NTF in a sample from a control subject not having heartburn or other symptoms of GERD can be a predetermined amount. Thus, the presence or absence of an increase in the amount of E-cadherin NTF in the sample of a subject can be compared to a predetermined amount of E-cadherin NTF in a sample from a subject not having heartburn or other symptoms of GERD, wherein the presence of an increase in the amount of E-cadherin NTF identifies a subject as having an increased likelihood of a rapid relapse of GERD after or subsequent to reducing the dosage of or terminating or ending PPI therapy.

Accordingly, a subject in which E-cadherin CTF is detected or an increase in E-cadherin NTF is detected would be a subject at increase risk for a rapid relapse of GERD upon reduction in the dosage of the PPIs or upon termination of PPI therapy. Such a subject would be maintained on the PPI therapy whereas a subject having no detectable E-cadherin CTF (i.e., wherein an absence of E-cadherin CTF is detected) or no increase in E-cadherin NTF (i.e., wherein an absence of an increase in E-cadherin NTF is detected) would be a subject for whom PPI therapy could be reduced or terminated without the concern that they would have a rapid relapse of GERD.

In other embodiments of the present invention, a method of identifying a subject as having an increased likelihood of a rapid relapse of GERD after reducing the dosage of or terminating proton pump inhibitor therapy is provided comprising detecting the presence or absence of E-cadherin C-terminal fragments (CTF) in a sample (e.g., stratified squamous epithelial tissue) from said subject, wherein the presence of E-cadherin CTF in said sample identifies the subject as having an increased likelihood of a rapid relapse of GERD after reducing the dosage of or terminating proton pump inhibitor therapy Thus, in embodiments of the present invention, the presence or absence of an increase in the amount of E-cadherin CTF in a sample (e.g., stratified squamous epithelial tissue) of a subject is compared to the level of E-cadherin CTF in a sample (e.g., stratified squamous epithelial tissue) from a control subject not having heartburn or other symptoms of GERD (i.e., chest pain, dysphagia, cough, throat clearing, hoarseness and/or wheezing). The level of E-cadherin CTF in a sample from a control subject not having heartburn or other symptoms of GERD can be a predetermined amount. In some embodiments, said predetermined amount can be zero. Thus, the presence or absence of E-cadherin CTF in a sample from a subject can be compared to a predetermined amount of E-cadherin CTF in a sample from a subject not having heartburn or other symptoms of GERD, wherein the presence of E-cadherin CTF identifies a subject as having an increased likelihood of a rapid relapse of GERD after reducing the dosage of or terminating/ending PPI therapy.

An additional aspect of the present invention provides a method of identifying a subject as having an increased likelihood of a rapid relapse of GERD after reducing the dosage of or terminating proton pump inhibitor therapy comprising detecting the presence or absence of an increase in the amount of E-cadherin CTF in a sample (e.g., stratified squamous epithelial tissue) from said subject, wherein the presence of an increase in the amount of E-cadherin CTF in said sample identifies the subject as having an increased likelihood of a rapid relapse of GERD after reducing the dosage of or terminating/ending PPI therapy.

In further aspects of the invention, the presence or absence of an increase in the amount of E-cadherin CTF in a sample (e.g., stratified squamous epithelial tissue) from a subject is compared to the level or amount of E-cadherin CTF in a sample (e.g., stratified squamous epithelial tissue) from a control subject not having heartburn or other symptoms of GERD (i.e., chest pain, dysphagia, cough, throat clearing, hoarseness and/or wheezing). The level of E-cadherin CTF in a sample from a control subject not having heartburn or other symptoms of GERD can be a predetermined amount. Thus, the presence or absence of an increase in the amount of E-cadherin CTF in a sample from a subject can be compared to a predetermined amount of E-cadherin CTF in a sample from a control subject not having heartburn or other symptoms of GERD, wherein the presence of an increase in the amount of E-cadherin CTF in a sample from a subject identifies the subject as having an increased likelihood of rapid relapse of GERD after reducing the dosage of or terminating/ending PPI therapy and wherein the absence of an increase in the amount of E-cadherin CTF in said sample identifies the subject as having a reduced likelihood of a rapid relapse of GERD after reducing the dosage of or terminating/ending PPI therapy.

A still further aspect of the present invention provides a method of monitoring the healing of reflux esophagitis (i.e., a method of monitoring the healing of nonerosive esophagitis in a subject (whose lesion is reflected in the presence of dilated intercellular spaces on microscopy) or the healing of erosive esophagitis). Thus, the present invention provides a method of monitoring the healing of reflux esophagitis (i.e., erosive and/or nonerosive esophagitis) in a subject comprising: detecting the amount of E-cadherin N-terminal fragments (NTF) in a first sample (e.g., gastric juice, blood, urine, tears, saliva, and the like) from a subject prior to beginning treatment for reflux esophagitis; detecting the amount of E-cadherin NTF in a second sample (e.g., gastric juice, blood, urine, tears, saliva, and the like) from said subject at a time point after treatment for reflux esophagitis has begun; and comparing the amount of E-cadherin NTF in said first and second samples, whereby a decrease in the amount of E-cadherin NTF between the first sample and the second sample indicates the healing of reflux esophagitis in said subject. Such monitoring can be done in conjunction with or without the use of esophagogastroduodenoscopy.

Thus, in some embodiments, a sample is obtained from a subject identified as having reflux esophagitis (i.e., erosive or nonerosive esophagitis) prior to treatment for reflux esophagitis and the amount of E-cadherin NTF in the sample is determined. The subject then begins treatment for reflux esophagitis (i.e., erosive or nonerosive esophagitis). After treatment is begun a further sample is obtained from the same subject and the amount of E-cadherin NTF in the further sample is determined. The amount of E-cadherin NTF in each sample is compared. A decrease over time in the amount of E-cadherin NTF indicates that the reflux esophagitis (i.e., erosive or nonerosive esophagitis) is healing.

Accordingly, a baseline level of E-cadherin NTF may be determined upon the initial diagnosis of reflux esophagitis (i.e., erosive or nonerosive esophagitis) and/or prior to the first treatment. After a baseline is established, the level of E-cadherin NTF may be determined repeatedly, e.g., on a regular schedule (e.g., once a week, once a month, once every two months, once every three months, once every four months, and the like). Thus, a patient can be monitored for healing at 1 week, 2 weeks 4 weeks, 6 weeks, 8 weeks, 10 weeks, 12 weeks, 14 weeks, 16 weeks, and the like. The present invention can be used to monitor subjects that are asymptomatic while under treatment to determine if the drug therapy can be reduced or ended (e.g., long term monitoring). Thus, a subject can be monitored monthly, every two months, every three months every four months, every five months, every six months and the like. A subject can be monitored yearly. Thus, the information obtained from the monitoring may be used to modify the treatment the subject is receiving.

Increased quantities of NTFs of E-cadherin are reported to be present in blood or urine in other disorders, in addition to GERD, including cancer (melanoma, gastric, colon, prostate, bladder, lung), multiorgan failure, sepsis, skin inflammatory disease (psoriasis, pemphigus vulgaris, eczema, atopic dermatitis, Darier's disease), Sjogren's disease, endometriosis (4-8). Any patients presenting with any of the above identified conditions would be readily recognizable, and excluded as having confounding effects on the test results for NTFs with respect to GERD. However, it is important to note that the methods of the present invention comprising detecting CTFs of E-cadherin, specifically in esophageal biopsies, can be used with patients presenting with any of the above identified conditions (for which NTFs of E-cadherin are reported in blood and/or urine) because E-cadherin CTFs are not reported in esophageal biopsies from subjects having these disorders.

It is further contemplated that the present invention provides kits for use in screening, diagnosing and identifying subjects with GERD, the kits comprising the compositions of this invention (e.g., antibodies for detection of E-cadherin fragments). It would be well understood by one of ordinary skill in the art that the kit of this invention can comprise one or more containers and/or receptacles to hold the reagents (e.g., antibodies, and the like) of the kit, along with appropriate buffers and/or diluents and/or other solutions and directions for using the kit, as would be well known in the art. Accordingly, in further embodiments, the present invention provides a kit for identifying a subject as having GERD, the kit comprising, consisting essentially of, or consisting of (a) antibodies to E-cadherin NTF and/or E-cadherin CTF; and (b) written instructions for methods for identifying a subject as having GERD comprising detecting the presence or absence of E-cadherin CTF in a sample and/or detecting the presence or absence of an increase in the amount of E-cadherin NTF and/or E-cadherin CTF in a sample, and optionally additional reagents or apparatus for carrying out methods for detecting E-cadherin NTF and/or E-cadherin CTF.

In still further embodiments, the present invention provides a kit for identifying a subject as having heartburn or other symptoms of GERD (i.e., chest pain, dysphagia, cough, throat clearing, hoarseness and/or wheezing) that is responsive or non-responsive to proton pump inhibitor therapy, the kit comprising, consisting essentially of or consisting of (a) antibodies to E-cadherin NTF and/or E-cadherin CTF; and (b) written instructions for methods for identifying a subject as having heartburn or other symptoms of GERD that is responsive or non-responsive to proton pump inhibitor therapy comprising detecting the presence or absence of E-cadherin CTF in a sample and/or detecting the presence or absence of an increase in the amount of E-cadherin NTF and/or E-cadherin CTF in a sample, and optionally additional reagents or apparatus for carrying out methods for detecting E-cadherin NTF and/or E-cadherin CTF.

In aspects of present invention, a kit is provided for identifying a subject as having an increased likelihood of a rapid relapse of GERD after reducing dosage of or terminating proton pump inhibitor therapy, the kit comprising, consisting essentially of or consisting of (a) antibodies to E-cadherin NTF and/or E-cadherin CTF; and (b) written instructions for methods for identifying a subject as having an increased likelihood of a rapid relapse of GERD after reducing dosage of or terminating proton pump inhibitor therapy comprising detecting the presence or absence of E-cadherin CTF in a sample and/or detecting the presence or absence of an increase in the amount of E-cadherin NTF and/or E-cadherin CTF in a sample, and optionally additional reagents or apparatus for carrying out methods for detecting E-cadherin NTF and/or E-cadherin CTF.

In another aspect of present invention, a kit is provided for monitoring the healing of reflux esophagitis (i.e., erosive or nonerosive esophagitis) in a subject, the kit comprising, consisting essentially of, or consisting of (a) antibodies to E-cadherin NTF; and (b) written instructions for methods for monitoring the healing of reflux esophagitis in a subject comprising: (i) detecting the amount of E-cadherin N-terminal fragments (NTF) in a first sample from a subject prior to beginning treatment for reflux esophagitis; (ii) detecting the amount of E-cadherin NTF in a second sample from said subject at a time point after treatment for reflux esophagitis has begun; and (iii) detecting the presence or absence of an increase in the amount of E-cadherin NTF in a sample; and (c) optionally additional reagents or apparatus for carrying out methods for detecting E-cadherin NTF.

The present invention will now be described with reference to the following examples. It should be appreciated that this example is for the purpose of illustrating aspects of the present invention, and does not limit the scope of the invention as defined by the claims.

EXAMPLES

Example 1

The pathogenesis of GERD is accepted as arising from prolonged contact of EE with refluxed gastric hydrochloric acid (HCl), and the accuracy of these concepts supported by the enormous success of PPI therapy, both in controlling heartburn and other symptoms of GERD and healing erosions. Yet, given the presence of physiologic reflux and the fact that healthy subjects experience no heartburn during esophageal acid perfusion (Bernstein test), it is evident that not all acid contact with EE is damaging, and this in part a testament to defenses within the esophageal epithelium (EE) itself. Among the more important of these intrinsic defenses is the barrier function of EE (9). This is performed by the apical membranes of surface cells within stratum corneum and adjacent apical junctional complexes (AJCs) that guard the paracellular (shunt) pathway. The cells of stratum corneum have been shown to represent the barrier layers, as evidence by their collective ability to block diffusion of lanthanum into the cells or intercellular spaces with either luminal or serosal application (10). And though diffusion into the intercellular space was blocked by cell-cell contacts considered to be TJs, their capacity for barrier function remains uncertain due to the paucity of strands and grooves present at such contacts.

The ability of the barrier in esophageal epithelium (EE) to resist acid damage can be shown experimentally by monitoring the total transepithelial electrical resistance ($R_T$) in Ussing chambered rabbit EE (11, 12). Thus, exposure to luminal (or serosal) HCl as low as pH 2.0 results in no change in $R_T$, while luminal (or serosal) HCl, pH<2.0, breaks the barrier as shown by a precipitous fall in $R_T$ (13), a fall confirmed to represent an increase in paracellular permeability (PCP) by circuit analysis, paracellular flux, and morphologic appearance of dilated intercellular spaces (DIS) on transmission electron microscopy (TEM) (12, 14). This increase in PCP is highly significant because it threatens the viability of EE by enabling luminal HCl to more freely diffuse into and acidify the intercellular space and adjacent basolateral cell membranes. Acidification of basolateral membranes is of concern because it contains an ion-gradient driven, Na-independent Cl/HCO3 exchanger (15, 16), that converts the low extracellular pH (pHo) into a low intracellular pH (pHi) by CF entry and $HCO_3$-removal from the cell (13, 17). Low pHi in turn raises intracellular calcium ($Ca^{++}$) and this induces cell swelling by stimulating excess osmolyte uptake by a basolateral bumetanide-sensitive, NaK2Cl cotransporter (18, 19). That a similar pattern occurs when luminal HCl contacts and damages human EE is supported by the fact that: a) in vivo esophageal perfusion with HCl, pH 1.1, both precipitates heartburn (+Bernstein) and lowers the in vivo electrical potential difference (PD) in NERD, the latter a reflection of the decline in $R_T$ (20), b) esophageal perfusion with HCl, pH 1.1, in vivo leads to development of dilated intercellular spaces (DIS) (21), c) DIS is present in EE of GERD, both NERD and erosive esophagitis (22-24) and d) DIS correlates with heartburn in GERD and resolves with heartburn upon treatment with PPIs (22). Taken together, the results indicate that heartburn develops in GERD when an increase in paracellular permeability (PCP) (as evidenced by acid-induced lowering of PD and development of DIS) enables luminal acid sufficient access to trigger the firing of nociceptors within EE as illustrated in FIG. 2 (25). Further, since human EE, like rabbit EE, has a basolateral Na-independent, $Cl/HCO_3$ exchanger (26), the lowering of intercellular pH can lower pHi, risking cell injury and necrosis, which are the precursor lesions to macroscopic erosions.

Although the initial damage upon contact of luminal acid with EE was established to be an increase in PCP, it was unclear whether the damage was a direct effect of acid contact with the apical junctional complex or an indirect effect of junctional opening mediated by a lowering of pHi. This question was addressed by monitoring pHi using pH microelectrodes implanted in surface cells in intact EE during exposure to pH 1.6 and observing that when $R_T$ declined, pHi declined and stabilized at 6.527. However, when the pHi of the same surface cells was lowered to pH 6.5 by serosal exposure to HCl, pH 3.0, there was no decline in $R_T$. Hence, the break in the barrier (i.e., decline in $R_T$ at luminal pH 1.6) was the cause of the decline in pHi and not the effect of a decline in pHi. This was consistent with the conclusion that luminal acid directly attacked and damaged the apical junctional complex leading to the increase in PCP. Further supporting this conclusion was the observation that luminal acid-induced cell necrosis could be prevented using a cell-impermeant, serosal buffer (HEPES) (28) as a replacement for bathing solution bicarbonate or, that cell swelling and necrosis could be prevented in rabbit EE exposed serosally to HCl, pH 2.0, by pretreatment serosally with 4 mM 4-acetoamido-4'-isothiocyanostilbene-2,2'-disulfonic acid (SITS) (a disulfonic stilbene derivative, that blocks the acid-absorbing, basolateral membrane Na-independent, Cl/HCO3 exchanger) (13). Further, protection by serosal HEPES occurs without preventing the luminal acid-induced increase in PCP (i.e., reduction in $R_T$). Thus, luminal acid directly attacks and damages the apical junctional complex, and the resulting increase in PCP promotes cell necrosis, first by acidifying the intercellular space and then by lowering pHi via basolateral membrane Na-independent, $Cl/HCO_3$ exchange.

Example 2

The Barrier Function of Esophageal Epithelium

The Apical Cell Membrane.

The esophageal epithelium (EE) lacks a surface mucus-unstirred water layer rich in $HCO_3^-$ to neutralize back diffusing $H^+$ (9). Consequently, its first major defense is the barrier function of the EE, the latter created by the apical cell membranes and AJCs. Although the apical cell membranes are designed to keep luminal $H^+$ from diffusing directly into the cell, its lipid bilayer contains an amiloride-insensitive, cation channel, designed for $Na^+$ aborption (29, 30). This channel, however, is non-selective, permitting $K^+$ and $Li^+$ to diffuse through it as well as $Na^+$. Though this raised the concern that $H^+$ could also traverse it, monitoring pHi in surface cells suggested that this was not the case since even pHo of 2.0 did not change pHi (27). To examine this process in greater detail, a Ussing chamber (U-chamber) model was created in which $Na^+$ passage through the channel could be monitored in rabbit EE as a current (Isc). This was done by adding nystatin serosally to permeabilize the basolateral membrane and abolish the spontaneous short circuit current (Isc). A $Na^+$ current was then created by establishing a 10:1 lumen-to-serosa $Na^+$ gradient (30). Also, incremental acidification of the luminal bath from pH 7.0 to pH 2.0 results in a fall in current, starting at pH 3.5, and progressing so that at pH 2.0 the current is effectively abolished. Only when pH is <2.0 and the barrier is broken is an increase in current observed as $H^+$ and $Na^+$ diffuse along their concentration gradients from lumen-to-serosa. These results indicate that the cation channel in EE is pH-sensitive and capable of shutting down its transport route under conditions of high luminal acidity that could pose a threat to cell survival—a process that may be viewed in EE as a form of protective adaptation against acid injury.

The Apical Junctional Complex (AJC).

The AJC also participates in barrier function by limiting diffusion of luminal $H^+$ into the intercellular space of EE. A tripartite structure, the AJC consists of tight junctions, adherens junctions and desmosomes. The most luminal member of the AJC is the tight junction (TJ). The TJ encircles the cell and regulates movement of ions and molecules through the paracellular (shunt) pathway (31, 32). Claudins and occludin are the transmembrane components of the TJ, and these connect to the scaffold proteins, Zonula occludens-1,2&3 (ZO1, ZO2 & ZO-3). ZO-1,2,3 in turn connect the claudins/occludin to the cytoskeleton by binding to actin microfilaments. The claudins, a 24-member superfamily with two extracellular loops, gained prominence by their diversity and ability to form a network of strands and grooves characteristic of the TJ (32-34). To better define the TJ in human EE, quantitative polymerase chain reaction (qRT-PCR) was performed for 21 claudins in biopsies of healthy EE and the results compared to another EE, Barrett's esophagus (35). In squamous EE, 11 of 21 claudins were quantifiable but small in amounts. The two most prominent, based on ZO-1 as reference of 1.0, were claudins 1 and 4, at 0.5 and 0.7, respectively. Western blots (W-blots) showed that protein levels paralleled gene expression and immunohistochemistry showed distinctive distributions, with claudin 4 in cell membranes of all except the most basal layer and claudin 1 in basal and middle layers but absent from stratum corneum. TJ morphology in human EE on TEM was similar to rabbit EE (10), with TJs, appearing as brief 'kisses' and with freeze fracture failing to show any of the typical strands and grooves at cell-cell contacts.

Below the TJ is the adherens junction (AJ), a structure that encircles the cell and initiates and stabilizes cell-cell adhesion, and by doing so, the AJ supports the barrier function of the TJ (36, 37). The single-pass, transmembrane protein of the AJ is the $Ca^{++}$-dependent E-cadherin (E-cad) and this connects directly to a group of catenins ($\alpha$-catenin, $\beta$-catenin, p120-catenin), which in turn connect E-cad to the cytoskeleton via $\alpha$-catenin's interaction with actin microfilaments, to the microtubules via p120-catenin's interaction with PLEKHA7/nezha and tubulins (38, 39), and to the TJ via p120-catenin's binding to ZO-136. Cell-cell adhesion by E-cad results from the $Ca^{++}$-dependent, homotypic, association between the extracellular domains of neighboring cells. Indeed, the $Ca^{++}$ sensitivity is so characteristic that it forms the basis of the '$Ca^{++}$-switch technique' where $Ca^{++}$ removal from both bathing solutions results in junctional opening (decline in $R_T$) and its restoration results in 'resealing' (recovery of $R_T$) (40). This method was used to define the role of E-cad in junctional adhesion in EE (41). Removing $Ca^{++}$ lowered $R_T$ by about 35% over 2 hrs while restoration returned $R_T$ to baseline (41). Resealing, was found to be specific for $Ca^{++}$, concentration-dependent and dependent on extracellular, but not intracellular, $Ca^{++}$. Further, resealing was also shown to be dependent on E-cad because it was inhibited by antibodies (HECD-1, DECMA-1) or small synthetic peptides to its extracellular (N-terminal) domain of E-cad, but not by 0.002% vs 0.0004 antibodies (4A2C7) to its intracellular (C-terminal) domain (41). Immunohistochemistry using HECD-1 showed E-cad in cell membranes of all layers of EE, and colocalization with $\beta$-catenin shown in primary cultures of human EE. These data establish that E-cad, through the association of its $Ca^{++}$-dependent extracellular domains, plays a key role in junctional adhesion and that this process has a direct effect on junctional barrier function—the latter shown by a fall in $R_T$ and increase in fluorescein flux (in $Ca^{++}$-free soln=0.0020±0.002% versus 0.00040±0006% in normal Ringer, n=4, p<0.05).

Desmosomes (DEs) are the most distal components of the apical junction complex (AJC). Unlike, the TJ and AJ, they form "spot welds" designed for tissue stability. Their transmembrane proteins are the cadherins, desmoglein and desmocollin (42, 43). They bind to desmoplakins in the membrane, which in turn bind to the cytoskeleton via intermediate filaments composed of cytokeratins. Since dilated intercellular spaces (DIS) do not encircle the cell, they do not directly participate in barrier function; however, DEs do participate indirectly by maintaining close apposition of the lateral cell membranes (LCMs), The LCMs, contribute to $R_T$, as resistors to the flow of ions/molecules across the multilayered EE by framing the long, narrow, serpiginous shunt pathway. Thus, the LCMs were recently found to be the major $Ca^{++}$-independent component of shunt resistance (Rs) and one that is sensitive to luminal hypertonicity and insensitive to $Ca^{++}$ removal. Thus, luminal exposure of rabbit EE to hypertonic urea could produce DIS and an increase in fluorescein flux but without disrupting the AJ, indicating that the junctional, $Ca^{++}$-dependent, resistance of the AJ and the hypertonicity-dependent resistance of the LCMs were in series, i.e. $Rs=R_{AJ}+R_{LCM}$. That the DEs were linked to resistance of the LCMs was shown by the reduction in $R_T$ and production of DIS when EE was exposed to empigen, a detergent, that disrupts the DE-cytokeratin network. It is noted that although desmogleins/desmocollins are cadherins and so reportedly are $Ca^{++}$-sensitive, both the literature (44, 45) and the experience of the present inventors with the $Ca^{++}$-switch (41) indicate that their $Ca^{++}$ sensitivity is limited to newly formed contacts, as in wound healing, and does not apply to the 'mature' DE.

The TJ and AJ are both connected to actin microfilaments, but only the AJ is connected to the microtubule network (38, 39). Thus, the junctional resealing during the $Ca^{++}$-switch technique was inhibited by the microfilament destabilizer, cytochalasin D, 2 uM (46). Yet, resealing was also inhibited by the microtubule destabilizer, colchicine, 10 mM (46), and further, junctional opening by $Ca^{++}$-free soln was inhibited by the microtubule stabilizer, taxol, 50 µM (46). Inhibition of resealing by taxol is appreciated by normalizing the data at the end of junctional opening in $Ca^{++}$-free solution. Thus, these findings reinforce the importance of the AJ and E-cad in junctional adhesion and barrier function in EE.

Example 3

Barrier Breakers in Refluxate, Meals & Inflammation

Barrier Breakers.

Agents that increase paracellular permeability (PCP) in EE are potential contributors to GERD by enabling diffusion of luminal acid into the intercellular space. Therefore, substances were sought within the refluxate, meals and inflammation that could 'break the barrier'. This was done by exposing rabbit EE in U-chambers to candidate inflammatory agents while both monitoring $R_T$, as a marker of PCP, and Isc (short circuit current), as a marker of active transport. The inflammatory agents were selected based on presence in EE or on reports that they can break the barrier in other epithelia (47-60).

Interestingly, aside from high luminal acidity, the only barrier breakers identified were: pepsin at pH 2, taurocholic acid at pH 2, and at pH 7.4: alcohol, heat, hypertonicity and trypsin. It is noteworthy that trypsin can break the barrier since it can be present within refluxates of near-neutral pH when patients with GERD are on PPI therapy (61-63). PPIs control acidity, but not reflux, and so trypsin is in position to maintain the junctional damage initiated by acid reflux prior to PPI therapy. Interestingly, luminal trypsin damages the junction in a similar manner as luminal acid in that it results in both DIS (61) and cleavage of E-cad's extracellular domain. A role for trypsin in reflux esophagitis in vivo has been suggested by the ability of the trypsin inhibitor, camostat mesilate (64, 65), to reduce esophagitis in a rat model of reflux and in patients with duodeno-esophageal reflux post-gastrectomy.

Dilated Intercellular Spaces (DIS).

Dilated intercellular space is a marker of increased PCP. When luminal acid damages rabbit EE, there is an increase in PCP accompanied by the development of DIS (12). This same lesion is identified in both erosive and non-erosive forms of GERD (24).

The physicochemical basis for DIS was investigated and it was found that for expression, the lesion required a high concentration of luminal HCl with luminal $H^+$ being needed to break the barrier and luminal $Cl^-$ needed to create an osmotic force to draw water into the intercellular space (66). Further, the barrier could be broken and the intercellular space (ICS) diameter increased with 100 mM HCl, but not with 100 mM choline chloride. In addition, the increase in ICS diameter that accompanies 100 mM HCl could be prevented by abolishing the $Cl^-$ gradient (i.e. by addition of 100 mM choline chloride to the serosal bath). Furthermore, as with 100 mM HCl, the barrier could be broken with 50 mM $H_2SO_4$ and yet ICS diameter did not increase, this is because of the failure of the larger ($SO_4^=$) anion to diffuse in sufficient amounts to osmotically draw excess water into the intercellular space (66). Thus, the data reveal that DIS (increase in ICS diameter) reflects the presence of a break in the barrier, but that a break in the barrier can be present in the absence of DIS.

This observation is notable since it shows that when DIS (and heartburn) resolve on PPI therapy, they can do so without a guarantee that the broken barrier has been healed. Consequently, PPI therapy can control heartburn by removal of $H^+$ access to the nociceptors and resolve DIS by removal of the CF gradient for water movement, while potentially trypsin or other products, within a refluxate of near-neutral pH, silently maintains the junctional damage. Indeed, the damage remains silent until PPI therapy is stopped, restoring acid reflux and $H^+$ access to the esophageal nociceptors across the broken barrier. That the barrier remains broken in patients controlled on PPIs has support from a study showing that the Bernstein (esophageal acid perfusion) test can remain (+) while on (67) or after successful treatment with PPIs, and that the speed of onset of heartburn (as marker of a broken barrier) is a better predictor of relapse than the occurrence of pathologic reflux on pH monitoring. The target of luminal acid is E-cadherin. Luminal HCl, pH<2.0, directly attacks and damages the EE, leading to a decline in $R_T$ and increase in PCP. Although $R_T$ is a complex function, $[R_T=(Ra+Rb)(Rs)/Ra+Rb+Rs$; where a=apical membrane, b=basolateral membrane, s=shunt resistance], circuit analysis shows that the decline in $R_T$ reflects a decline in Rs (12). In these studies it was found that $Rs=R_{AJ}+R_{LCM}$, where the former is the $Ca^{++}$-sensitive resistor (the AJ) (40), and the latter is the hypertonicity-sensitive resistor (the LCMs) (68). Thus, these differences were used to better define the locus of attack by luminal HCl. This was done by sequentially exposing rabbit EE (first) to $Ca^{++}$-free soln and then (second) to either hypertonic urea, 500 mM, or HCl, pH 1.6.

The results show that after $R_T$ is reduced by $Ca^{++}$-free soln, that exposure to luminal hypertonic urea further reduces $R_T$; however there is no further reduction in $R_T$ upon subsequent exposure to luminal HCl (i.e. the hypertonicity, but not HCl, has an additive effect on $R_T$). Thus, the findings indicate that luminal acid and $Ca^{++}$-free solution share the same target, E-cad (i.e., both reduce $R_T$ by reducing $R_{AJ}$, and since $R_{AJ}$ reflects adhesion by E-cad, the results indicate that the target of acid is E-cad).

That adhesion by E-cad is altered at acidic pH is also shown and illustrated by: a) the ability of luminal HCl, pH 2.0 but not pH 3.0, to inhibit resealing in the $Ca^{++}$ switch technique; and b) the ability of the microtubule stabilizer, taxol (46), to inhibit junctional opening by exposure to luminal pH 1.6, just as it was noted for $Ca^{++}$-free solution. The latter is particularly notable since the AJ, not the TJ, is linked to the microtubule network (38, 69-71), reinforcing the concept that the target of luminal acid is E-cad and that damage to E-cad accounts for the increase in PCP.

Further, the nature of the damage to E-cad was sought by exposing rabbit EE in U-chambers to luminal HCl, pH 1.1, for 30 min. After incubation of EE in organ culture for 4 hrs, W-blots, using a C-terminal monoclonal antibody (4A2C7) showed that E-cad was cleaved. Based on the size of the C-terminal fragment (CTF) of about 25 kD, referred to as CTF2, the site of cleavage was extracellular and close to the cell membrane, and so likely to be due to cleavage by a metalloprotease (MP) or γ-secretase, with cleavage by these two enzymes, often occurring sequentially (MP followed by γ-secretase), a process referred to as RIPping (72, 73). This proved correct in that cleavage of E-cad (by exposure to either luminal HCl, pH 1.1, for 30 min, or serosal HCl, pH 2.0, for 5 min) was blocked by the metalloprotease inhibitor, Marimastat (74), 10 μM.

Interestingly, though the γ-secretase inhibitor, 10 μM DAPT75 (Calbiochem, N.J.) did not block cleavage, it did change the pattern of cleavage, yielding two CTFs instead of one. The smaller CTF, called CTF2, is similar to that observed in acid-exposed EE without inhibitors, and a second CTF, called CTF1, of higher molecular weight that is consistent with cleavage by a metalloprotease. A similar pattern occurs in knockouts of presenilin-1 (PS1), the equivalent of γ-secretase, in mouse embryos. Here, CFT1 emerges in the absence of PS1, while in its presence only CTF2 is observed (75). These results are consistent with initial cleavage of E-cad by an acid activated MP that is rapidly followed by cleavage by γ-secretase, accounting for the observed CTF2 on the W-blot in uninhibited acid-exposed EE. In effect, it is only by inhibiting γ-secretase that metalloprotease activity becomes apparent.

The possibility that acid-induced cleavage of E-cad was the result of apoptosis (76, 75) was considered unlikely given the 25kD size of the CTF, its abolition by Marimastat, and lack of effect on acid-induced cleavage by an inhibitor of caspase 3, 50 μM Z-DVED-FMK (77) (Calbiochem, N.J.). A similarly negative outcome was found when apoptosis was sought as an explanation for disruption of the AJ in a model of intestinal inflammation (59). Consequently, these findings support E-caderin as the target of attack and damage by luminal acid and further support that the damage becomes irreversible because of cleavage of its extracellular domain by a MP.

Example 4

Barrier Function in GERD

Barrier Function of Human EE.

There is a paucity of data on the structure and function of healthy human EE. This is because it is difficult to obtain EE in sections large enough for mounting in standard-sized U-chambers (aperture 1.13 cm$^2$). However, as technology improved, mini-U-chambers have become became available with an aperture of only 0.0314 cm$^2$, suitable for mounting endoscopic biopsies (about 3 mm). This enabled the study and comparison of the electrical properties of two types of EE, one being native squamous EE and the other Barrett's epithelium (78). The study showed that squamous EE in Ringer solution had a relatively high RT and low Isc while Barrett's had a low $R_T$ and high Isc. Squamous EE, being primarily a $Na^+$ absorbing tissue, was also highly sensitive to $Na^+$ removal and to ouabain, while Barrett's absorbed $Na^+$ and secreted anions (chloride/bicarbonate) in almost equal amounts. These results document that the mini-U-chamber is suitably robust to identify in biopsy-sized specimens differences in transport and barrier function in EE.

Accordingly, data from such studies show that biopsies of NERD have significantly lower $R_T$ (69±5 ohms·cm$^2$ versus 217±80 ohms·cm$^2$, n=5, p<0.05) and higher fluorescein flux (0.2040±0.1500% veresus 0.0126±0.0090%, n=4, p<0.05) than subjects with healthy EE, supporting the concept that the EE in NERD/GERD have an increase in PCP as explanation for the prior finding of the presence of DIS (24).

(1) The Apical Junctional Complex (AJC) in GERD.

In order to identify the cause for the increase in PCP (and thus DIS) in GERD, the TJ was examined on TEM but no structural abnormalities were noted. Next, using qRT-PCR, the claudin profiles in biopsies from healthy EE were compared to those with NERD and erosive esophagitis, n=3/group. Using ZO-1 as a reference, the only significant difference that emerged, after comparing 20 claudins and occluding, was a decrease in claudin-4. On W-blot, claudin 4 was also reduced but neither claudin 1, claudin 4 nor occludin was cleaved. In the only report to date, a rat model of reflux esophagitis, found that claudin 3 was reduced, claudin 1 increased and both claudin 4 and occludin had shifted from membrane to cytoplasm (as shown by immunohistochemistry) (79).

(2) Adherens Junction (AJ).

Since the target of attack and damage by luminal acid in rabbit EE is E-cad, E-cad was assessed in biopsies of EE from 6 patients with GERD (3 with erosive esophagitis and 3 with NERD). Although qRT-PCR showed that E-cad expression was increased in GERD, on W-blots, E-cad was cleaved in GERD but not in healthy EE (FIG. 3A). Based on the size of a CTF of about 35 kD, corresponding to CTF1 in rabbit EE, the site of cleavage was extracellular, close to the membrane, and consistent with cleavage by a MP. Further, the expression of γ-secretase was markedly downregulated in GERD and was consistent with the appearance in GERD of CTF 1 (rather than CTF2 as in the rabbit model or for mouse embryos as reported by Marambaud et al, (FIG. 3B) (75).) This finding was compatible with the emergence of CTF1 in PS1 knockouts in mouse embryos shown in FIG. 3B or treatment with the γ-secretase inhibitor in rabbit EE. Also, in GERD, the metalloprotease, Adam-10, was modestly increased on qRT-PCR, and Adam-10 protein expression (using a polyclonal antibody, Chemicon, MA) was shown to switch from the inactive form to the active form in both NERD and erosive esophagitis on W-blot. In addition, a lack of colocalization of Adam-10 and E-cad was observed in GERD. Thus, Adam-10 was shown to be expressed in membranes using immunohistochemistry but these same membranes were largely devoid of E-cad. In addition, consistent with cleavage of E-cad in GERD was the presence of increased quantities of 'jettisoned' NTFs in blood (Mean±±0.13 vs. GERD=2.05±0.10, n=9-10/gp, p<0.0001).

Thus, these findings support the increase in PCP in GERD as being the result of cleavage of the extracellular domain of E-cad by the metalloprotease, Adam-10. Further, since CTFs of E-cad and increased quantities of NTFs of E-cad are detectable in biological samples, they can be used as biomarkers of GERD in the clinical setting.

Example 5

General Methods

Rabbit Model.

Models of acid-activated cleavage of E-cad can be generated in two ways: 1) by luminal exposure to HCl, pH 1.1, for 30 min, and 2) by serosal exposure to HCl, pH 2.0, for 5 min. Serosal exposure is the most efficient means of cleavage because it mimics chronic acid exposure, recapitulating what occurs after luminal HCl, pH 1.1, breaks the barrier and acidifies the intercellular space and basolateral cell membranes. Following exposure, EE is washed in Ringer solution, pH 7.4, and placed in a Petri dish containing Dulbecco's Minimum Essential Medium (DMEM) with high glucose (4.5 g/l), supplemented with 2% FCS, 1 mM Na pyruvate, 2 mM/1 L-glutamine, 5 μg/ml insulin, 5 μg/ml transferrin, 0.01 μg/ml hydrocortisone and 0.01 μg/ml cholera toxin. After incubation for 4 hrs at 37° C. in 5% CO2/95% O2 in high humidity, EE is processed for CTF by W-blot using a C-terminal monoclonal antibody (4A2C7) to E-cad (Zymed, Carlsbad, Calif.). In instances where NTFs of E-cad are sought, after exposure, EE is incubated in serum free DMEM for 4 hrs and the supernatant processed by ELISA or W-blot using an N-terminal monoclonal antibody (HECD-1) to E-cad (Zymed, Carlsbad, Calif.). For Adam-10 detection a monoclonal antibody (Zymed, Carlsbad, Calif.) is used; and W-blots performed.

Human Biopsies.

Up to 8 esophageal biopsies are obtained from the lower 5 cm of esophagus in each patient. Those for determination of CTF are immersed in RNAlater (Ambion, Austin, Tex.) until ready for processing by W-blot using a C-terminal monoclonal antibody (4A2C7) to E-cad (Zymed Labs, San Francisco, Calif.).

Blood Sample.

A peripheral venous blood sample, 5-10 cc, is obtained using an anticoagulant-free red top tube. After clotting, the sample is spun down and serum removed and stored frozen at −20° C. Detection of NTFs of E-cad (soluble E-cad) is by commercial Human E-cadherin EIA Kit (Zymed, Carlsbad, Calif.) according to the manufacturer's instructions. Detection relies on a sandwich technique in which an N-terminal monoclonal antibody to E-cad (HECD-1) is bound to the base of 96-well plates. This antibody binds NTFs of E-cad in serum and the amount quantitatively determined by addition of a second tagged-N-terminal monoclonal antibody whose reaction is read fluorimetrically. Purified E-cad is provided as part of the kit for the generation of a standard curve and from which units of fluorescence of the sample are converted to quantity of NTFs (soluble E-cad) in μg/ml. Note that the values reported in the literature for healthy controls (and so disease states) vary widely depending on the manufacturer of the kit and among kits of the same manufacturer (4, 87-90), Consequently according to the manufacturer's directions, "Each laboratory should establish its own normal range for soluble E-cadherin level."

Statistics.

Parametric data are compared using Student's t-test for paired or unpaired samples. Non-parametric data for differences in frequency or prevalence of normal/abnormal test results between two populations are compared using the Chi square 2×2 contingency table or Fisher exact test. Sensitivity, specificity, (−) predictive value and (+) predictive value will be calculated for each population and receive operating curves used to optimize cutoff values for (+) and (−) test results.

Example 6

Clinical Studies

Increased quantities of NTFs of E-cad are reported to be present in blood in other disorders including cancer (melanoma, gastric, colon, prostate, bladder, lung), multiorgan failure, sepsis, skin inflammatory disease (psoriasis, pemphigus vulgaris, eczema, atopic dermatitis, Darier's disease), Sjogren's disease, endometriosis (4-8). Thus, patients with any of the above identified conditions are excluded from participation in the studies outlined herein.

Defining the Accuracy of Identifying CTF of E-Cad in Biopsies and Elevated Quantities of NTFs in Blood for the Diagnosis of GERD.

Data indicate that patients with GERD, but not healthy subjects, have cleaved E-cad in biopsies. In addition, patients with GERD have significantly higher quantities of NTFs of E-cad in blood compared to healthy subjects. Also, there is no apparent difference between the values for NERD and erosive eosphagitis; this lack of difference is not unexpected since both NERD and erosive esophagitis have DIS, a marker of junctional damage in GERD on TEM.

Esophageal biopsies and blood are obtained from patients with GERD (NERD, n=25, and erosive disease, n=25) and subjects with a healthy esophagus, n=25. GERD is diagnosed by a history of heartburn at least 3 time per week plus either erosions on EGD, abnormal 24 hr pH monitoring (total acid exposure >4% in 24 hrs), and/or relief of heartburn on PPIs (relief=no heartburn for 6-7 days and only mild one day/week). Those with a healthy esophagus will have no history of esophageal symptoms and no abnormality on EGD and biopsy. Samples are analyzed without knowledge of group.

Biopsies are evaluated for presence or absence of CTF of E-cad with a (+) CTF indicative of GERD. Serum values are quantified for NTFs and analyzed such that a patient whose value is greater than two times the standard error of the mean for simultaneously run controls is considered to have a (+) test for GERD. Based on this approach, the data yields a sensitivity of 100% and a specificity of 90% for the diagnosis of GERD. From these results, a receiver operating characteristic (ROC) curve is generated to identify the optimum cutoff value for maximizing sensitivity and specificity for the diagnosis of GERD. Subgroup analyses are also performed to determine if differences emerge between those with NERD or erosive esophagitis and controls. Because sensitivity and specificity vary depending on disease prevalence, ROC curves are generated for each subgroup. Densitometry is employed on W-blots as an alternative means of discriminating between those positive and negative for GERD.

CTFs in Biopsies and Elevated Quantities of NTFs of E-Cad in Blood as Biomarkers for Distinguishing Between Patients with Heartburn Responsive to PPIs and Patients with Heartburn Unresponsive to PPIs.

Subjects with heartburn and a negative EGD have a relatively low (about 50%) response to PPIs (106, 107). This attributed to those with PPI-refractory disease having heartburn that is either unrelated to NERD (e.g., functional heartburn), or mediated in NERD by a pathway other than acid exposure (e.g., visceral hypersensitivity or sustained esophageal contractions) (25, 108-110). In either case, these data indicate that heartburn, as a presenting symptom, lacks specificity for the diagnosis of GERD and for the presence of PPI-responsive heartburn. Nonetheless, heartburn historically suggests GERD, so that almost all are given PPI therapy. Unfortunately, the drugs are often continued, even for those that are unresponsive to PPIs, and paradoxically, at higher doses to ensure that acid secretion has been adequately suppressed.

Therefore, it will be determined whether those with PPI-responsive heartburn have an acid-mediated event, and so likely have (+) cleavage of E-cad, while those with PPI-unresponsive heartburn have non-acid-mediated symptoms and thus have symptoms unassociated with cleavage of E-cad. Tests that detect products of cleavage of E-cad should prove valuable in distinguishing between these groups and thereby help in determining the appropriateness of initiating and/or maintaining PPI therapy.

Biopsies and blood are obtained from those with EGD-neg heartburn responsive to PPIs, n=25, and with esophagogastroduodenoscopy (EGD)-negative heartburn that is unresponsive to PPIs, n=25. Heartburn unresponsive to PPIs is present when heartburn occurs ≥3 times/wk while on PPIs twice/day ≥2 months]. Samples are processed for CTFs of E-cad in EE and quantity of NTFs of E-cad in blood as in Example 5, above. Samples are analyzed without knowledge of category and comparisons made between PPI-responsive and PPI-unresponsive groups with respect to sensitivity, specificity, and (+) and (−) predictive value.

Detection of CTFs in Biopsies and Elevated Quantities of NTFs of E-Cad in Blood as Biomarkers to Distinguish Between Patients with Esophagitis Due to GERD and Patients with Esophagitis Due to Other Causes.

Patients with heartburn, odynophagia, dysphagia and chest pain often have EGD and biopsies that yield a diagnosis of 'esophagitis'. Yet, in many instances, the specific etiology remains unclear. Causes of esophagitis include: GERD, eosinophilic esophagitis, pill-induced esophagitis (e.g., NSAIDs, bisphosphonates, KCl tablets, vitamin C, tetracycline, etc.), lye and infectious esophagitis (*Candida*, *Herpes*, cytomegalovirus, AIDS). The most difficult to distinguish between are GERD and pill-induced esophagitis. It can also be difficult to distinguish between eosinophilic esophagitis and GERD, since both can have tissue eosinophilia. Thus, the present experiments are carried out in order to determine if acid-mediated cleavage of E-cad in esophagitis can be used to distinguish GERD from eosinophilic and/or pill-induced esophagitis.

Esophageal biopsies and blood are obtained from subjects with an abnormal EGD due to erosive esophagitis, eosinophilic esophagitis and pill-induced esophagitis, n=25/group, and processed for CTFs of E-cad in EE and NTFs of E-cad in blood as previously described. Diagnoses are based on standard clinical criteria. Samples are analyzed without knowledge of etiology and comparisons made between erosive esophagitis (of GERD) and esophagitis of other etiologies with respect to sensitivity, specificity, and (+) and (−) predictive value.

Detection of Elevated Quantities of NTFs of E-Cad in Blood can Serve as a Biomarker to Distinguish Between Patients Who Relapse Rapidly after Stopping PPIs and Patients Whose Relapse is Delayed after Stopping PPIs.

PPI therapy controls, but does not cure, GERD. Data indicate that this can occur because of failure of the EE to heal. Notably, the consequence of failure to heal is rapid relapse upon PPI cessation, resulting in maintenance on PPIs for years, if not for life. Since rapid relapse implies the persistence of damage to the junctions in EE, perhaps due to exposure to trypsin in refluxates of near neutral pH, detection of elevated quantities of NTFs of (soluble) E-cad in blood may identify those with a broken barrier that is prone to rapid relapse upon stopping PPIs. Conversely, those without elevated levels of NTFs are more likely to have a healed EE and so would more likely remain asymptomatic for an extended period after stopping PPIs.

Blood samples are obtained from patients with GERD, n=50, with heartburn controlled on PPIs (i.e., no heartburn for 6 of 7 days/week and at most only mild heartburn one day/week for ≥6 months) and the samples processed for NTFs of E-cad. PPIs are then discontinued (antacids for mild symptoms permitted) and a diary of frequency and severity of heartburn is kept. Phone follow up is monthly and clinic visits are quarterly for 1 year. Symptom relapse is declared if heartburn (mild) occurs ≥3×/wk, heartburn (moderate) occurs 2×/wk, heartburn (severe) occurs at any time or the patient declares the symptoms troublesome enough to prompt them to resume PPI therapy. Time to relapse is documented and frequency of elevated levels of NTFs compared for relapsers and non-relapsers at 6 months. Sensitivity, specificity, and (+) and (−) predictive value are determined.

Also, to determine if ongoing non-acid reflux is the cause of the failure of the barrier to repair, NTFs of E-cad are quantified in blood of patients who had heartburn controlled by fundoplication, n=20 patients. Lower levels of NTFs in the fundoplication group as compared to the PPI-controlled population, supports ongoing non-acid reflux as the cause of the failure of the barrier to repair.

Quantification of NTFs of E-Cad in Blood as a Biomarker to Monitor the Healing of Erosive Eosphagitis without the Need for EGD.

Patients with erosive esophagitis routinely undergo follow up EGD to monitor the healing of EE on PPI therapy. Since the data presented herein indicate that patients with GERD have increased quantities of NTFs of (soluble) E-cad in biological samples (e.g., blood, urine, tears, gastric juice, saliva) as compared to controls, the quantity of NTFs in biological samples may be useful for monitoring the healing of erosive esophagitis without the need for repeat EGD. To assess this possibility, biological samples are obtained initially from those with heartburn and erosive esophagitis on EGD, n=25, and a repeat biological sample is obtained on return for follow up EGD, typically 12-16 weeks later. Samples are processed without the knowledge of when they are obtained and the quantity of NTFs is determined for all before and after samples in a single run of a 96 well-test kit, the latter to allow direct comparison of absolute values before and after endoscopic healing by the paired Student's t test.

Example 7

Endoscopic Biopsies of EE from GERD: Characterization of Junction Barrier Function and Correlation of Defects with Changes in E-Cadherin E-cadherin is a component of the adherens junction, a structure known to be important in junctional barrier function in most epithelia, including that of the esophagus (36, 41, 121). It is a single-span, transmembrane protein whose carboxy (C)-terminus resides in the cytoplasm and whose amino (N)-terminus resides in the intercellular space. The N-terminus of E-cadherin molecules from membranes of adjacent cells form a barrier by calcium-dependent binding to each other within the intercellular space. Since the protein bridges of E-cadherin both encircle the cell membrane and support the adhesion of the bridging proteins (occludin and claudins) forming the tight junction, they play an integral role in establishing junctional (electrical) resistance and controlling junctional permeability. This role for E-cadherin in (rabbit) EE has recently been shown in the Ussing chamber using the calcium-switch technique (41). This technique reveals that removing bathing solution calcium lowers $R_T$ and restoring calcium returns $R_T$ to baseline; however, this return of $R_T$ to baseline after restoration of calcium can be prevented in EE by exposure to antibodies (or short peptides) to the extracellular, but not intracellular, domain of E-cadherin. These results support a role for E-cadherin in the junctional barrier in EE and suggest that any increase in junctional permeability in the EE in GERD may be accounted for by disruption in its bridge formation.

All subjects were adults, aged 18-75 years old, that were undergoing endoscopy for clinical reasons. Biopsies were obtained of grossly-normal appearing mucosa from the lower 5-cm of esophagus using jumbo forceps (Radial Jaw-3 Maximum Capacity, Boston Scientific, Natick, Mass.). Subjects with symptomatic GERD had a history of heartburn in association with typical esophageal erosions (erosive esophagitis) or a history of heartburn and either pathologic acid exposure on 24 hr pH monitoring or positive response to proton pump inhibitor therapy (NERD). Control subjects with a healthy esophagus had no history of esophageal symptoms (heartburn, regurgitation, dysphagia, odynophagia) nor endoscopic signs of esophageal disease. Venous blood samples were obtained by venipuncture using a red top tube without preservatives from the same subjects. All patients provided written, informed consent for these procedures, and the study was approved by the Human Research Ethics Committee of University of North Carolina at Chapel Hill.

Biopsies for chamber studies were immersed in ice-cold oxygenated Ringer solution and immediately transported to the laboratory for mounting mucosal side up in mini-Ussing chambers as previously described (78). These chambers have Lucite rings whose aperture is 2 mm in diameter and whose square area is 0.0314 cm$^2$. Biopsies were bathed on both sides with 5 ml of normal Ringer solution (composition in mmol/l): Na$^+$ 140, Cr 119.8, K$^+$ 5.2, HCO$_3^-$ 25, Ca$^{2+}$ 1.2, Mg$^{2+}$ 1.2, HPO$_4^{2-}$ 2.4, H$_2$PO$_4^-$ 0.4, 268 mosmol/kgH$_2$O, pH 7.4 when gassed with 95% O$_2$-5% CO$_2$ at 37° C. Two sets of electrodes connected the solutions in the chamber to voltage clamps (Voltage Current Clamp, MC6; Physiologic Instruments, San Diego, Calif.) that permitted the direct recording of the transmural electrical PD and determination of short-circuit current (Isc) by passage of current (Isc is recorded in µA/cm$^2$ and converted to µeq·cm$^{-2}$·h$^{-1}$ by multiplying by 0.0373). Total electrical resistance ($R_T$) was calculated using Ohm's law, where PD=Isc×$R_T$. All experiments were conducted under open-circuit conditions except when periodically switched to the short-circuit state for recording of Isc. The n value for each experiment represents the values obtained from one tissue per subject. After equilibration for 30 min, basal electrical readings of PD, Isc, and $R_T$ were obtained.

The transmucosal flux of fluorescein, 300 MW (Sigma, St. Louis, Mo.) was determined by adding 1 mM fluorescein to the luminal bath. After mixing, the luminal bath was sampled to obtain the initial fluorescein concentration. The serosal bath was sampled at zero time before fluorescein addition to the luminal bath and at periodic intervals following the addition of fluorescein to the luminal bath. Fluorescein levels in samples were determined by measuring sample fluorescence using a fluorometer (Turner biosystems, TBS-380 Amico SPF 500, Sunnyvale, Calif.). The flux was calculated as a percent of the luminal fluorescein concentration by dividing serosal fluorescein levels by the luminal fluorescein concentration times 100. The values for fluorescein recorded yield fluorescence values that are linear over the recorded range.

Methods for Western blotting, immunofluorescence and digital image processing were previously described (Jovov et al., 2009) (35). Antibodies against the intracellular carboxy (C)-terminus of human E-cadherin (Catalog#33-4000); and antibodies against mouse E-cadherin (Catalog#13-1900) were purchased from Zymed Laboratories (San Francisco, Calif.). Antibodies against the (C)-terminus of ADAM 10 were purchased from Millipore (Catalog#AB19026; Billerica, Mass.). Secondary antibodies for Western blots were goat anti-rabbit IRDye 800 (Rockland, Gilbertsville, Pa.) and goat anti-mouse Alexa 680 (Molecular Probes, Carlsbad, Calif.). Signals were detected using an Odyssey Infrared Imaging System (LI-COR, Inc., Lincoln, Nebr.).

Soluble (N-terminus) E-cadherin levels were measured in serum using a commercially available sandwich ELISA kit (Invitrogen, Carlsbad, Calif.). In brief, a monoclonal antibody to E-cadherin is coated on to microtitre plates. Samples containing an unknown amount of E-cadherin are incubated in the wells at 37° C. for 2 hours. A second, detecting, monoclonal antibody (conjugated with peroxidase) is incubated in the wells at 37° C. for 1 hour. Peroxidase substrate solution ($H_2O_2$ and tetramethylbenzibine) is added and results in a color change. The reaction is terminated by the addition of 1M $H_2SO_4$ and absorbance of the sample measured using a microtitre plate reader at 450 nm. Each sample is measured twice and the average value used for determination of E-cadherin concentration from a standard curve plotted using values obtained from standard solutions provided with the kit.

Deletion of E-Cadherin in Adult Mouse Esophagus.

The mouse line with an E-cadherin$^{flox}$ allele was derived by Boussadia (111) and maintained on a C57Bl/6 genetic background. No abnormal phenotype was observed in unrecombined homozygotes at any stage. To establish the keratin5 promoter driving CreER (KRT5-CreERT) transgenic mouse line, DNA was injected into fertilized zygotes. Offspring of 11 founders were screened to obtain two lines, one of which has expression in both trachea and esophageal basal cells (112) and the other which has expression in esophageal basal cells but not in tracheal cells. This second line, presently on the N3 backcross to C57BL/6, was used for current experiments. For adult lineage tracing, 8-10-week-old mice hemizygous for KRT5-CreERT and homozygous for R26R were injected intraperitoneally one time or four times every other day with Tamoxifen (Tmx), 0.25 mg/g body weight, in Mazola corn oil (ACH Food Companies, Memphis, Tenn.). To delete E-cadherin four times of TMX injection were performed every other day on KRT5-CreERT; E-cadherin$^{flox/flox}$ compound mutants and KRT5-CreERTE-cadherin$^{flox/+}$ control mice. Five days after the final tamoxifen injection, the esophagi were harvested, divided into three portions and processed as follows: one section for fixation in 4% paraformaldehyde for immunohistochemistry, one section for fixation in RNA-Later for ribonucleic acid (RNA) extraction and quantitative reverse transcriptase-polymerase chain reaction (qRT-PCR—see below), and one section placed in oxygenated-Ringer solution for mounting in mini-Ussing chambers and performance of fluorescein flux as described for human esophageal epithelium above. Xgal staining was performed as previously described (113, 114).

qRT-PCR. qRT-PCR was performed using previously described methods (115). In brief esophageal epithelial tissue underwent total RNA isolation using RNeasy kits (Qiagen, Inc., Valencia, Calif.) per the manufacturer's recommended protocols. RNA was treated with TURBO DNase (TURBO DNA-free kit, Ambion, Inc., Austin, Tex.) to remove contamination by genomic DNA. cDNA was synthesized from 2.5 µg of treated RNA for each cell culture sample using Superscript III reverse transcriptase (Invitrogen Corporation, Carlsbad, Calif.) with an equal amount of RNA included in a No-RT control for each separate RNA sample. Real-time PCR primers used in this study were validated primer sets (QuantiTect Primers Assays, Qiagen, Inc., Valencia, Calif.). Amplification was performed in a Rotor-Gene 3000 (Corbett Research, Mortlake, Australia) thermal cycler at 95° C. for 3 min followed by 37 cycles of 94° C. for 15 seconds, 54° C. for 20 seconds, and 72° C. for 25 seconds. Following amplification, a melting curve analysis was performed by heating the reactions from 50 to 99° C. in 0.2° C. intervals while monitoring fluorescence. The cycle at which each sample crossed a fluorescence threshold, Ct, was determined and triplicate values for each cDNA averaged.

Data are reported as the mean±standard error (SE); and statistical significance determined by Student's t-test for paired and unpaired samples at the $p<0.05$ level.

Example 8

Junctional Permeability is Increased in GERD

Biopsies of intact EE from GERD in mini-Ussing chambers revealed at equilibrium baseline values for $R_T$ that were significantly lower than those in controls (FIG. 4A). Further, transmucosal fluorescein fluxes performed on the same tissues over a 2 hr period yielded significantly higher fluxes in GERD than in controls (FIG. 4B). Both of these values are compatible with the EE in GERD having an increase in junctional permeability over that of healthy EE.

E-Cadherin is Cleaved in EE from GERD Patients.

Figure 5:
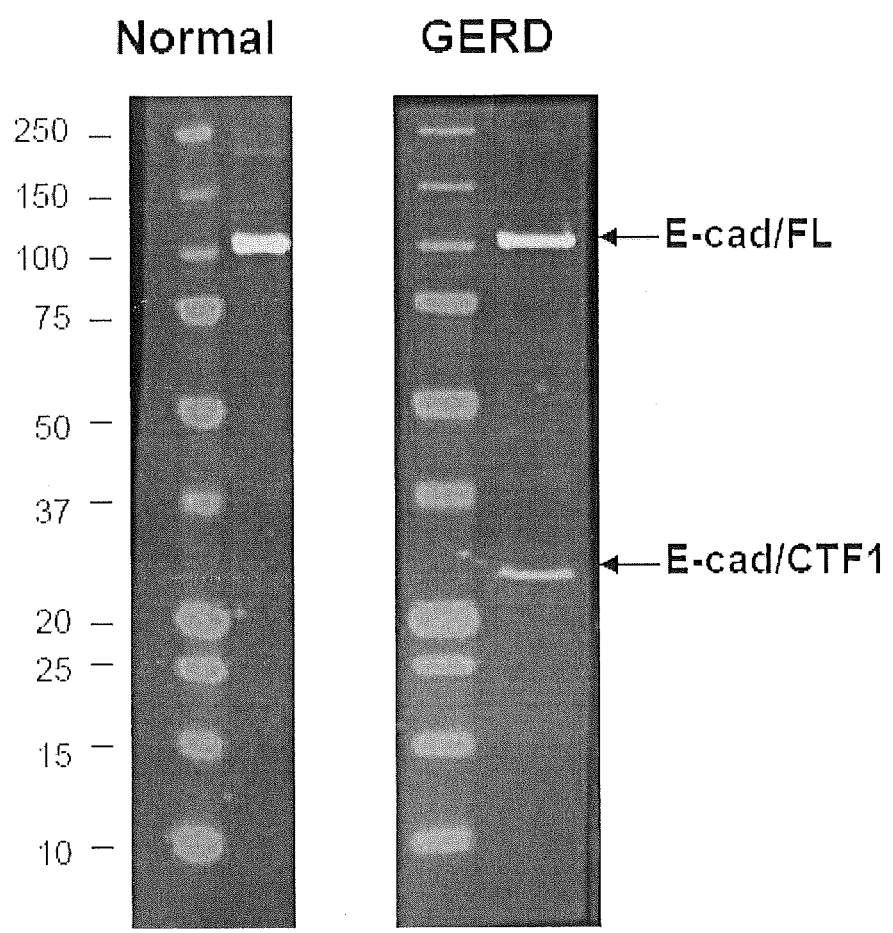
FIG. 5. Western blots of E-cadherin are shown for esophageal epithelium (EE) from patients with GERD and from subjects with a healthy esophagus (controls). Ten micrograms of protein are loaded in each lane and immunostaining for E-cadherin performed with a monoclonal antibody to a C-terminal epitope of human E-cadherin. Note that in control EE, there is a single band at 120 kilodaltons (kDa) while in GERD there are two bands, one at 120 kDa and a second at about 35 kDa. Molecular weight standards are displayed on the left and this immunoblot representative of 6 separate experiments performed using EE from different subjects.
Figure 6:
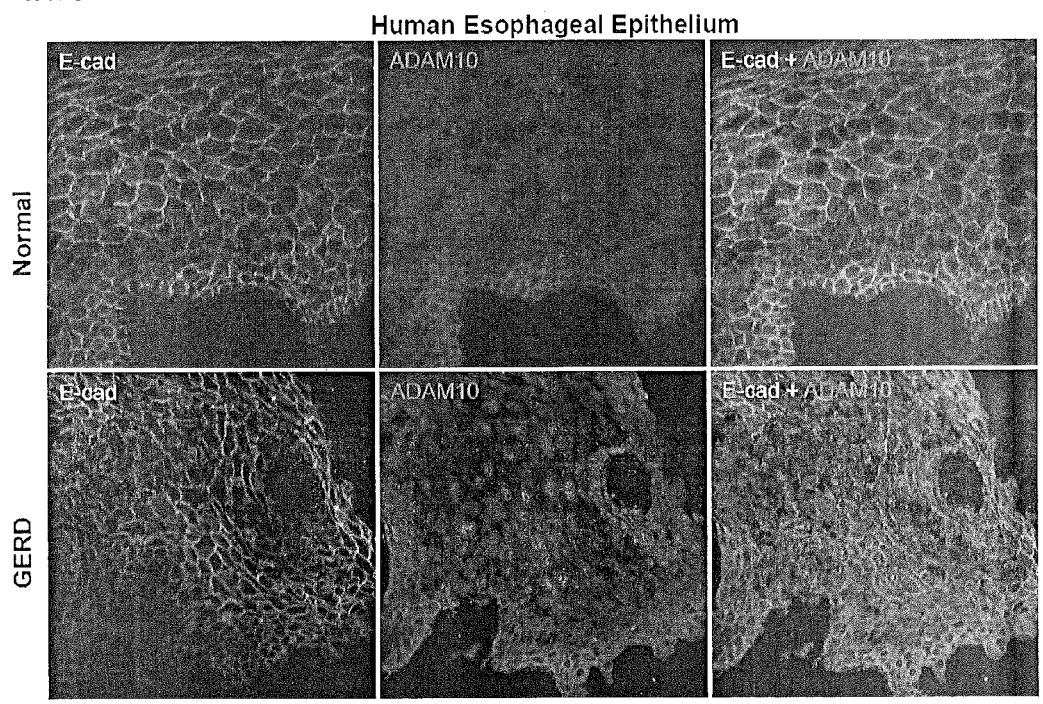
FIG. 6. Immunostaining for E-cadherin (red) and ADAM-10 (green) in esophageal epithelium (EE) from patients with GERD and from subjects with a healthy esophagus (controls). When colocalized, E-cadherin and ADAM-10 yield a yellow color. Immunostaining was performed using a monoclonal antibody to a C-terminal epitope of human E-cadherin and antibody to the C-terminus of ADAM-10. Note that the controls show widespread colocalization of the two molecules while in GERD wherever ADAM-10 is localized, there is no E-cadherin. This suggests that in GERD, the ADAM-10 was in active form and cleaved E-cadherin resulting in its removal from the area.

Western blots performed on EE from healthy controls using antibody to the C-terminus of E-cadherin revealed a single 120 kilodalton (KD) band compatible with an intact molecule. In contrast, the blots performed on EE from GERD yielded two bands, one at about 120 KD and one at about 35 KD. The presence of the C-terminal band at lower molecular weight indicates that in GERD some molecules of E-cadherin had been cleaved (FIG. 5). Immunostaining for E-cadherin using the same C-terminus antibody in healthy EE of controls demonstrated that E-cadherin was localized to the membranes of cells throughout all layers (FIG. 6, left upper panel). Notably, the size of the C-terminal fragment, 35 KD, indicated that E-cadherin was likely cleaved near the extracellular membrane, and one candidate for this cleaving activity is the membrane metalloproteinase A Disintegrin And Metalloproteinase (ADAM)-10.

Immunostaining for ADAM-10 documented its presence in healthy EE and showed that it colocalized with E-cadherin. In contrast, immunostaining for ADAM-10 in EE from GERD showed that E-cadherin was absent from those areas of EE in which ADAM-10 was highly expressed (FIG. 6). Since the lack of colocalization of ADAM-10 and E-cadherin in GERD suggested that E-cadherin may have been cleaved by an 'active' form of ADAM-10 and so depleted from those sites, 'active' Adam-10 was sought on Western blots (FIG. 2). Healthy EE exhibited 2 bands for ADAM-10, one band at 85 KD compatible with inactive ADAM-10 and a much less dense band at 60 KD representing an 'active' form of the molecule. Notably, the EE from GERD was devoid of the larger 85 KD band, which reflects the inactive form, while it exhibited a single dense band at 60 KD. This indicated that all of the ADAM-10 in EE from GERD was in the active form.

N-Terminal Fragments of Cleaved E-Cadherin are Increased in Serum of GERD Patients.

Figure 7:
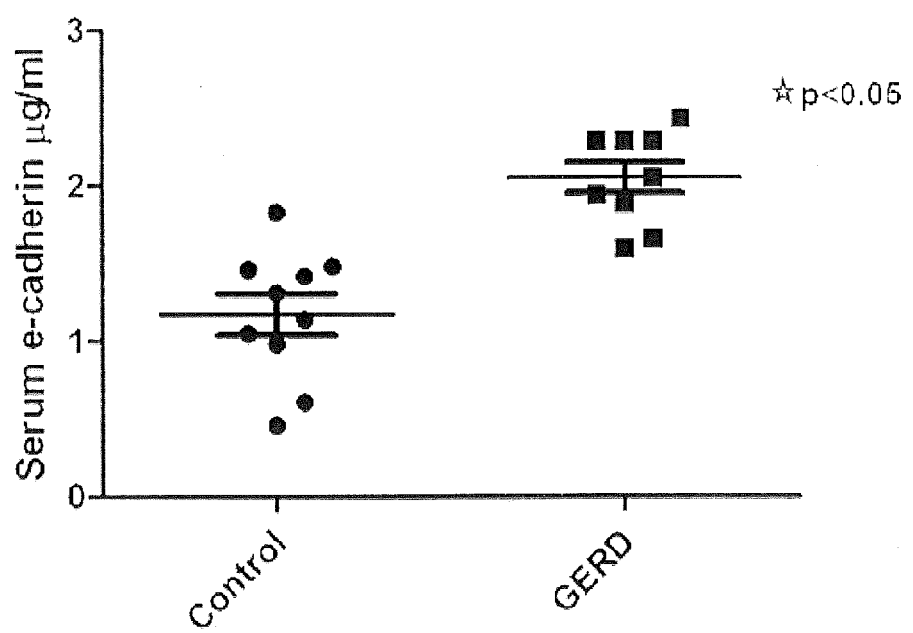
FIG. 7. ELISA using an N-terminal antibody to E-cadherin illustrates the quantity of soluble fragments of E-cadherin in serum of patients with GERD and in serum of subjects with healthy esophagus (controls). Significantly more N-terminal fragments are shown to be present in the serum in GERD. $*p<0.05$.

Cleavage of E-cadherin in EE from GERD results in loss of the N-terminal fragment of the molecule. Since the N-terminal fragment of E-cadherin is known to be soluble (116), we sought its presence in serum. Consistent with the finding of C-terminal fragments of E-cadherin in EE from GERD, serum levels of the N-terminal fragment were found to be significantly higher than that present in the sum of healthy controls (FIG. 7).

C-Terminal Fragments of Cleaved E-Cadherin are not Increased in Eosinophilic Esophagitis or in an Experimental Rabbit Model of Hyperosmotically-Induced Dilated Intercellular Spaces in Esophageal Epithelium.

DIS is a histopathologic feature of both erosive and nonerosive forms of GERD. As a marker of GERD, it is highly sensitive, with detection rates on transmission electron microscopy (TEM) ranging from 68-100% in esophageal biopsies from subjects with GERD. Although detection rates on TEM of biopsies from healthy subjects are low, ranging from 0-14%, its specificity for GERD has been questioned. This is because, in addition to appearing during luminal acid perfusion in humans and animals, DIS also occurs experimentally when rabbit esophageal epithelium (EE) is exposed luminally to hypertonic solutions and in rat EE under conditions of water-restraint stress. Moreover, and perhaps more clinically important, DIS are reported in EE from patients with eosinophilic esophagitis. Recently, a molecular event was identified, cleavage of E-cadherin, on Western blots that contributes to development of and so occurs in association with DIS in acid-exposed rabbit EE. Therefore, the specificity of E-cadherin cleavage as a biomarker for GERD was compared to that of DIS.

EE from 6 patients with GERD and 6 patients with eosinophilic esophagitis (diagnosed by application of standard clinical criteria) and from 3 rabbit EE exposed luminally to hypertonic urea at a concentration yielding DIS on TEM were obtained and immediately placed in RNA-Later. Western blots of EE were performed and E-cadherin detected using an antibody to the C-terminus end (FIG. 8).

Figure 8:
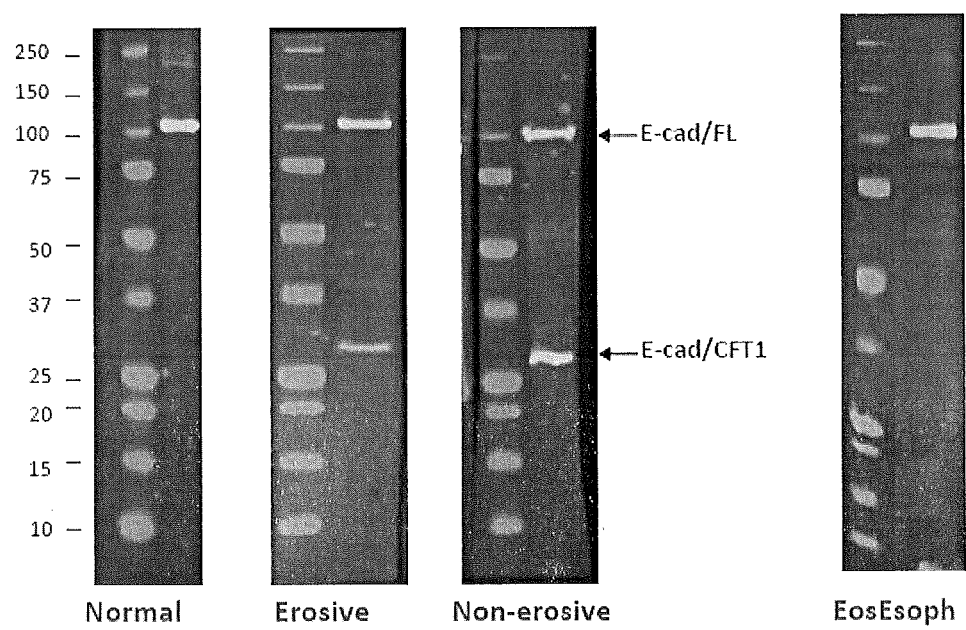
FIG. 8. Western blots of E-cadherin are shown for esophageal epithelium (EE) from patients with GERD (erosive and nonerosive), from subjects with a healthy esophagus (normal controls) and from patients with eosinophilic esophagitis (EosEsoph; far right bar). E-cadherin is not cleaved in eosinophilic esophagitis patients in contrast to the E-cadherin in patients having the two forms of GERD (erosive and nonerosive) and in normal controls, which also lack cleavage of E-cadherin.

Intact E-cadherin at about 120 kD was detected in all specimens; however, EE from GERD, but not EE from eosinophilic esophagitis or hypertonicity, revealed a cleaved (about 35 kD) fragment of e-cadherin (FIG. 8). Thus, cleavage of E-cadherin in EE is more specific than DIS as a biomarker of GERD. The ability to discriminate between GERD and eosinophilic esophagitis makes the detection of cleaved E-cadherin in EE clinically valuable.

Thus, these studies show that the presence of cleaved E-cadherin in esophageal biopsies (containing esophageal epithelium) distinguishes patients with gastroesophageal reflux disease from those with eosinophilic esophagitis, both of whom have the same histopathologic lesion on biopsies (i.e. dilated intercellular spaces within squamous epithelium). Moreover, cleaved E-cadherin in reflux patients also discriminates this lesion from that in an experimental model in which dilated intercellular spaces in stratified squamous epithelium is produced by exposing esophageal epithelium to hypertonic media such as hypertonic urea. In effect, cleavage of E-cadherin in esophageal biopsies is a superior marker for reflux disease than current morphologic markers of esophageal disease and can discriminate between two clinical disorders (reflux disease and eosinophilic esophagitis) that are known to overlap clinically and morphologically.

Conditional Deletion of E-Cadherin Increases Junctional Permeability.

Figure 9:
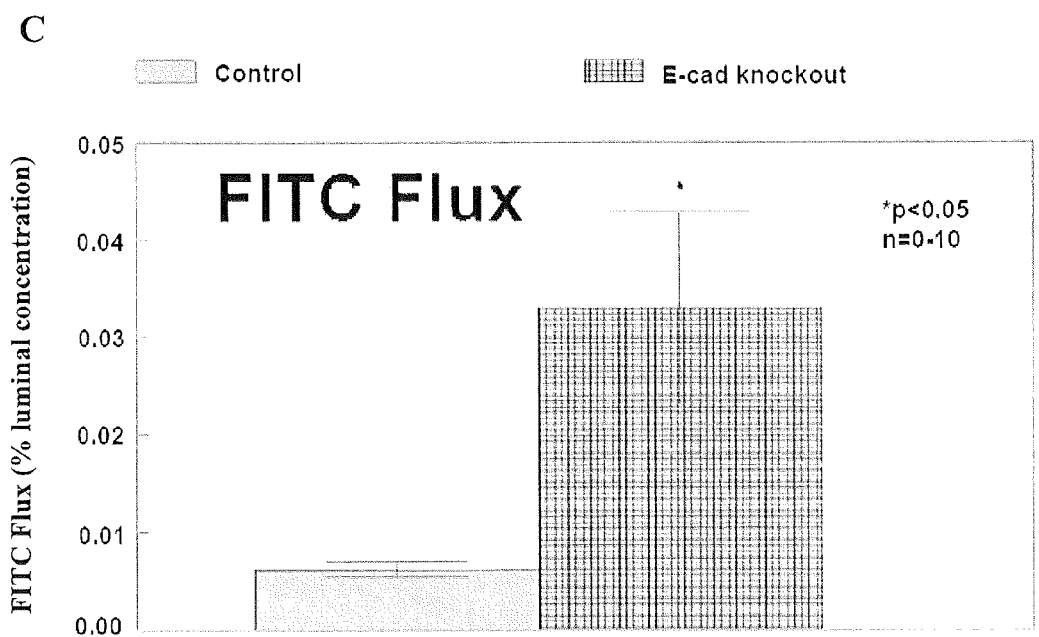
FIGS. 9A-C. (A) Quantitative RT-PCR for E-cadherin in adult mouse esophageal epithelium (EE). E-cadherin expression was measured 1 and 2 weeks after induction of gene deletion by tamoxifen. Results are expressed as percentage of ZO1 expression. (B) Immunolocalization in mouse EE for littermates (control), partial deletion model and full deletion model. Control panel demonstrates E-cadherin is localized to cell membranes of all layers while middle panel shows uneven staining of E-cadherin after partial deletion (7 days after tamoxifen injection) and right panel shows almost complete deletion at 2 weeks after tamoxifen induction. (C). Note that the mucosal-to-serosal fluorescein (FITC) flux in control EE is significantly lower than in the EE from the esophagus with complete deletion of E-cadherin. Values are means±SE. $*p<0.05$; n=8-10.

The data above indicate that the EE from GERD has increased junctional permeability and this occurs in association with cleavage of E-cadherin. To establish a cause-and-effect relationship between cleaved E-cadherin and junctional permeability, a model was developed in which E-cadherin was conditionally deleted from the adult mouse EE. This was done using a KRT5-CreERT mouse line in which a 6-kb human keratin 5 (KRT5) promoter was used to drive the expression of CreER fusion protein. A previously published Krt14-CreER transgenic line (Vasioukhin et al. Proc. Natl. Acad. Sci. 96(15):8551-8556 (1999), was also tried but no Cre recombinase activity was detected in the esophagus of adult Krt14-CreER; R26R mouse after multiple Tmx injections. Following the generation of KRT5-CreER; E-cadherin (E-cad$^{\Delta/\Delta}$ compound mutants and 5 days after performance of the last of 4 Tmx injections, little to no E-cadherin was detectable by qRT-PCR (FIG. 9A) or by immunostaining in the adult mouse EE (FIG. 9B). Despite the lack of E-cadherin expression, the EE was histologically normal. However, and consistent with an increase in junctional permeability, the EE with deleted E-cadherin had a significantly higher fluorescein flux than the EE from (untreated) littermate controls (FIG. 9C).

Figure 10:
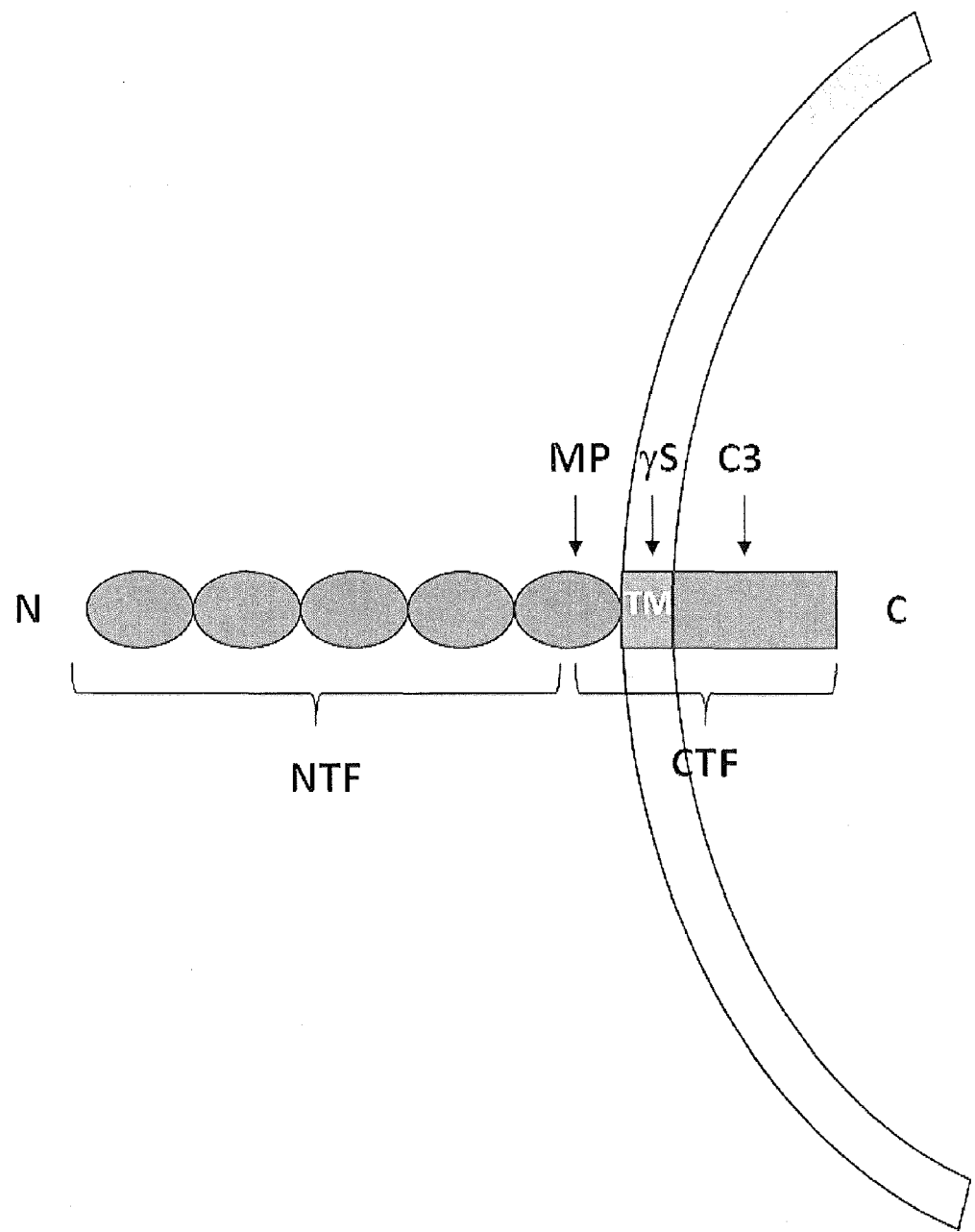
FIG. 10. Schematic representation of regulated intramembrane proteolysis (RIP) of E-cadherin. The E-cadherin molecule contains an extracellular N-terminal domain, transmembrane (TM) domain, and cytoplasmic C-terminal domain. Sequential cleavage of E-cadherin occurs by a process called RIPing, starting with a membrane metalloproteinase (MP) cleaving the extracellular domain, then followed by a membrane gamma-secretase cleaving within the membrane and finally by intracellular cleavage by cytosolic caspases, typically caspase-3. Notably, the cleaved extracellular N-terminal domain is soluble, diffuses into the blood stream and so can be measured in serum and other body fluids.

Nonerosive EE from GERD patients have lower $R_T$ and higher fluorescein flux than healthy EE. Since fluorescein is impermeant to (viable) cells and $R_T$ a sensitive marker of junctional integrity, these findings indicate that nonerosive EE in GERD have an increase in paracellular permeability. Moreover, we found that this increase in paracellular permeability in GERD was associated with cleavage of E-cadherin, the latter shown by the presence of two C-terminal bands in EE from GERD on Western blot. As illustrated in the diagram (FIG. 10), the larger 120 KD band represented intact E-cadherin and the 35 KD C-terminal band reflected a smaller, cleaved segment of E-cadherin. Consistent with cleavage of the N-terminal segment of E-cadherin in EE from GERD, the serum from GERD patients had higher amounts of soluble N-terminal fragments of E-cadherin than did healthy subjects. That healthy subjects have a measurable amount of N-terminal fragments of E-cadherin in serum reflects the fact that cleavage of E-cadherin is a physiologic process, reflecting cell turnover in such tissues as skin and kidney. Indeed, the phenomenon by which E-cadherin is cleaved has been studied and is known as regulated intramembrane proteolysis (RIP) or RIPing (117). RIPing occurs by activation of a set of proteolytic enzymes that cleave E-cadherin in stepwise fashion into ever smaller C-terminal fragments. As a result of cleavage, the extracellular (soluble) N-terminal fragment of E-cadherin is known to be jettisoned and absorbed into the blood stream (88, 89, 116, 118). Based on the 35 KD size of the C-terminal fragment identified in the EE from GERD, cleavage occurs close to the extracellular portion of the cell membrane—a site compatible with proteolysis by a membrane metalloproteinase (74, 96, 99) (FIG. 10).

In the present study, ADAM-10 was identified as a membrane metalloproteinase in human EE. Moreover, ADAM-10 was determined to be present in the EE from GERD only in its smaller and thus active form. That ADAM-10 in EE from GERD was in an active form was also supported on immunostaining by the lack of colocalization of ADAM-10 with E-cadherin. This supports that E-cadherin was cleaved by ADAM-10 and so was lost from its membrane location. Loss of E-cadherin from its membrane location in EE from GERD patients was further supported by the increased amounts of N-terminal fragments of E-cadherin present in the serum of GERD patients. Based on the process of RIPing, cleavage of E-cadherin by membrane metalloproteinases, e.g. ADAM-10, is followed sequentially by proteolytic cleavage of the C-terminal fragment by a membrane gamma-secretase and then by cytosolic caspases, typically caspase-3. Notably, each of these subsequent enzymatic actions, cleave the C-terminal fragment of E-cadherin into ever smaller components (75, 76, 119) (FIG. 10).

Example 9

A study was conducted in which 20 patients having active non-erosive reflux disease (NERD) were recruited based on the presence in the patients of moderate to severe heartburn while off acid suppressing medication and normal-appearing esophageal mucosa on upper endoscopy. Biopsies from the lower 5 cm of esophagus were obtained and available in 17 patients for performance of Western blots for E-cadherin. In addition, a peripheral venous blood sample was obtained from all 20 patients for quantitative determination of the N-terminal fragments (NTFs) of E-cadherin in serum by ELISA.

Western blots showed that 16 of the 17 patients with NERD had evidence not only of the 120 KD intact E-cadherin molecule but also a 36 KD C-terminal fragment (CTF) of E-cadherin in the biopsied esophageal epithelium. In contrast, though all controls (n=8) also had the 120 KD intact molecule of E-cadherin, none had evidence of E-cadherin cleavage in that there was no evidence of a lower molecular weight CTF. These data support the value of determining the presence of CTFs of E-cadherin in esophageal biopsies as a biomarker of active reflux disease.

Figure 11:
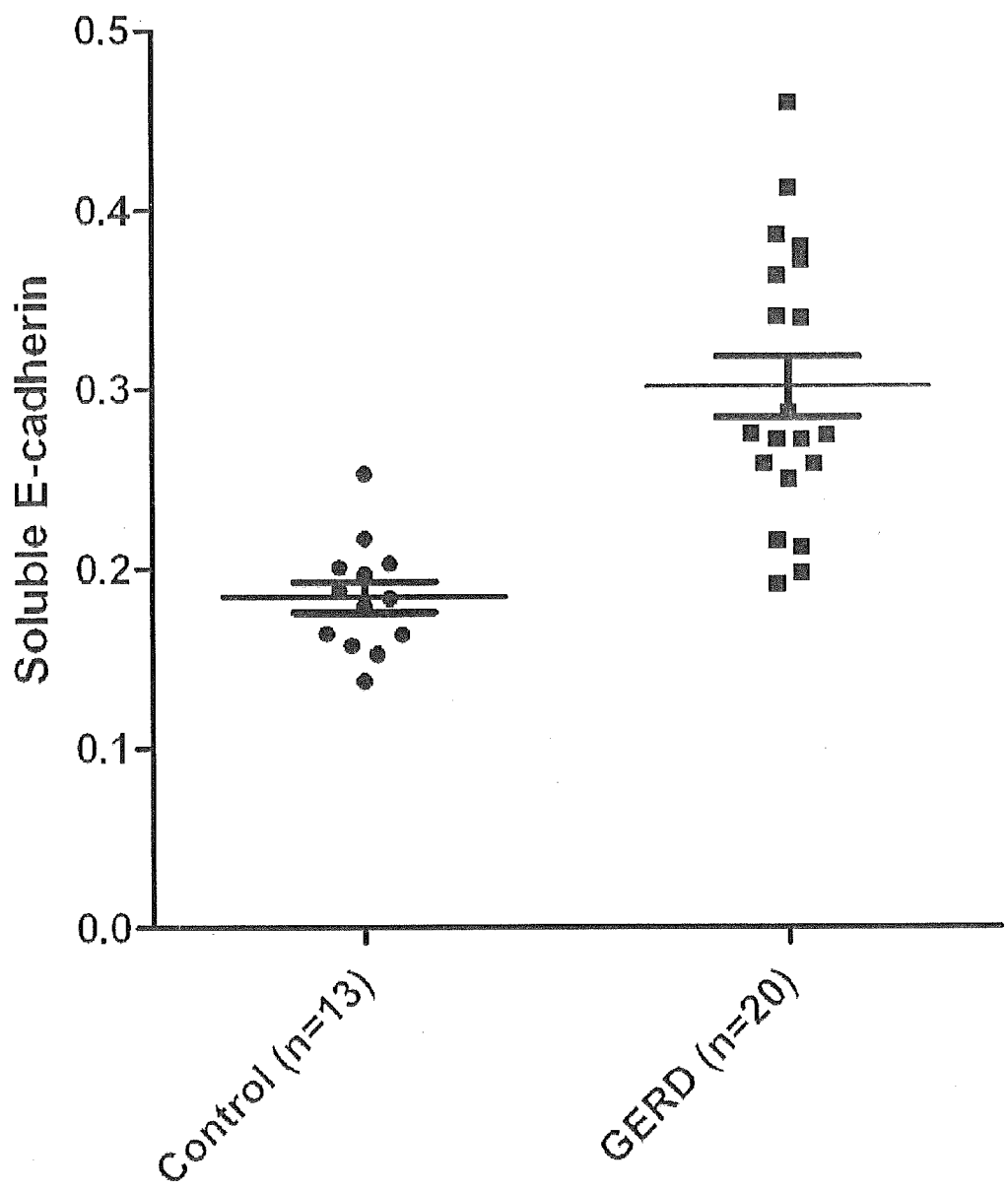
FIG. 11. Serum measurements of NTFs of soluble e-cadherin (in absorbance values) in 20 patients with NERD compared to 13 control subjects; $p<0.0001$.

The mean values for serum measurements of NTFs of E-cadherin (also known as soluble E-cadherin) were significantly elevated for the 20 patients with NERD compared to 13 control subjects, p<0.0001 (see FIG. 11 showing quantity of NTFs=soluble E-cadherin in absorbance values). It is also notable that using a value of >0.20 for absorbance gave a 90% sensitivity and 85% specificity for distinguishingNERD from controls based on the amount of NTFs of E-cadherin in serum. These data support the value of quantitatively determining serum NTFs of E-cadherin as a biomarker of active reflux disease.

Further supporting the value of using serum NTF quantitation as a biomarker of active reflux disease is that the inter-assay coefficient of variability (CV) calculated from the NERD population was shown to range from ~6-10%.

The foregoing is illustrative of the present invention, and is not to be construed as limiting thereof. The invention is defined by the following claims, with equivalents of the claims to be included therein.

All publications, patent applications, patents and other references cited herein are incorporated by reference in their entireties for the teachings relevant to the sentence and/or paragraph in which the reference is presented.

REFERENCES

1. Gerson L B, Fass R. A Systematic Review of the Definitions, Prevalence, and Response to Treatment of Nocturnal Gastroesophageal Reflux Disease. *Clin Gastroenterol Hepatol* 2008.
2. Fukuhara A, Irie K, Yamada A, Katata T, Honda T, Shimizu K, Nakanishi H, Takai Y. Role of nectin in organization of tight junctions in epithelial cells. *Genes Cells* 2002; 7:1059-72.
3. Masclee A A M D A, DeGraaf R, Cluysenaer O J J, Jansen J B M J. Ambulatory 24-hour pH-metry in the diagnosis of gastroesophageal reflux disease. *Scand J Gastroenterol* 1990; 25:225-230.
4. Jonsson M V, Salomonsson S, Oijordsbakken G, Skarstein K. Elevated serum levels of soluble E-cadherin in patients with primary Sjogren's syndrome. *Scand J Immunol* 2005; 62:552-9.
5. Fu C, Lang J. Serum soluble E-cadherin level in patients with endometriosis. *Chin Med Sci J* 2002; 17:121-3.
6. Cioffi M, Gazzerro P, Di Finizio B, Vietri M T, Di Macchia C, Puca G A, Molinari A M. Serum-soluble E-cadherin fragments in lung cancer. *Tumori* 1999; 85:32-4.
7. Pittard A J, Banks R E, Galley H F, Webster N R. Soluble E-cadherin concentrations in patients with systemic inflammatory response syndrome and multiorgan dysfunction syndrome. *Br J Anaesth* 1996; 76:629-31.
8. Matsuyoshi N, Tanaka T, Toda K, Okamoto H, Furukawa F, Imamura S. Soluble E-cadherin: a novel cutaneous disease marker. *Br J Dermatol* 1995; 132:745-9.
9. Orlando R C. Esophageal epithelial resistance. In: Castell D O, ed. *The Esophagus*. Boston: Little Brown Inc, 1995: 455-468.
10. Orlando R C, Lacy E R, Tobey N A, Cowart K. Barriers to paracellular permeability in rabbit esophageal epithelium. *Gastroenterology* 1992; 102:910-23.
11. Orlando R C. Mechanisms of acid damage to oesophageal epithelium: role of the paracellular pathway. *J Intern Med Suppl* 1990; 732:53-7.
12. Tobey N A, Hosseini S S, Argote C M, Dobrucali A M, Awayda M S, Orlando R C. Dilated intercellular spaces and shunt permeability in nonerosive acid-damaged esophageal epithelium. *Am J Gastroenterol* 2004; 99:13-22.
13. Tobey N A, Orlando R C. Mechanisms of acid injury to rabbit esophageal epithelium. Role of basolateral cell membrane acidification. *Gastroenterology* 1991; 101:1220-8.
14. Orlando R C, Powell D W, Carney C N. Pathophysiology of acute acid injury in rabbit esophageal epithelium. *J Clin Invest* 1981; 68:286-93.
15. Tobey N A, Reddy S P, Keku T O, Cragoe E J, Jr., Orlando R C. Mechanisms of HCl-induced lowering of intracellular pH in rabbit esophageal epithelial cells. *Gastroenterology* 1993; 105:1035-44.
16. Tobey N A, Reddy S P, Khalbuss W E, Silvers S M, Cragoe E J, Jr., Orlando R C. Na(+)-dependent and -independent Cl-/HCO3-exchangers in cultured rabbit esophageal epithelial cells. *Gastroenterology* 1993; 104:185-95.
17. Orlando R C. Gastroesophageal reflux disease: Offensive factors and tissue resistance. In: Orlando R C, ed. *Gastroesophageal Reflux Disease*. New York: Marcel Dekker, Inc, 2000:165-192.
18. Tobey N A, Koves G, Orlando R C. HCl-induced cell edema in primary cultured rabbit esophageal epithelium. *Gastroenterology* 1997; 112:847-54.
19. Tobey N A, Cragoe E J, Jr., Orlando R C. HCl-induced cell edema in rabbit esophageal epithelium: a bumetanide-sensitive process. *Gastroenterology* 1995; 109:414-21.
20. Orlando R C, Powell D. Studies of esophageal epithelial electrolyte transport and potential difference in man. In: Allen A, Flemstrom G, Garner A, Silen W, eds. *Mechanisms of Mucosal Protection in the Upper Gastrointestinal Tract*. New York: Raven Press, 1984:75-79.
21. Bove M, Vieth M, Dombrowski F, Ny L, Ruth M, Lundell L. Acid challenge to the human esophageal mucosa: effects on epithelial architecture in health and disease. *Dig Dis Sci* 2005; 50:1488-96.
22. Calabrese C, Bortolotti M, Fabbri A, Areni A, Cenacchi G, Scialpi C, Miglioli M, Di Febo G. Reversibility of GERD ultrastructural alterations and relief of symptoms after omeprazole treatment. *Am J Gastroenterol* 2005; 100:537-42.
23. Caviglia R, Ribolsi M, Maggiano N, Gabbrielli A M, Emerenziani S, Guarino M P, Carotti S, Habib F I, Rabitti C, Cicala M. Dilated intercellular spaces of esophageal epithelium in nonerosive reflux disease patients with physiological esophageal acid exposure. *Am J Gastroenterol* 2005; 100:543-8.
24. Tobey N A, Carson J L, Alkiek R A, Orlando R C. Dilated intercellular spaces: a morphological feature of acid reflux—damaged human esophageal epithelium. *Gastroenterology* 1996; 111:1200-5.

25. Barlow W J, Orlando R C. The pathogenesis of heartburn in nonerosive reflux disease: a unifying hypothesis. *Gastroenterology* 2005; 128:771-8.
26. Lao-Sirieix P, Corovic A, Jankowski J, Lowe A, Triadafilopoulos G, Fitzgerald R C. Physiological and molecular analysis of acid loading mechanisms in squamous and columnar-lined esophagus. *Dis Esophagus* 2008; 21:529-38.
27. Khalbuss W E, Marousis C G, Subramanyam M, Orlando R C. Effect of HCl on transmembrane potentials and intracellular pH in rabbit esophageal epithelium. *Gastroenterology* 1995; 108:662-72.
28. Tobey N A, Powell D W, Schreiner V J, Orlando R C. Serosal bicarbonate protects against acid injury to rabbit esophagus. *Gastroenterology* 1989; 96:1466-77.
29. Awayda M S, Bengrine A, Tobey N A, Stockand J D, Orlando R C. Nonselective cation transport in native esophageal epithelia. *Am J Physiol Cell Physiol* 2004; 287:C395-402.
30. Tobey N A, Argote C M, Awayda M S, Vanegas X C, Orlando R C. Effect of Luminal Acidity on the Apical Cation Channel in Rabbit Esophageal Epithelium. *Am J Physiol Gastrointest Liver Physiol* 2007; 292:G796-805.
31. Aijaz S, Balda M S, Matter K. Tight junctions: molecular architecture and function, *Int Rev Cytol* 2006; 248:261-98.
32. Angelow S, Yu A S. Claudins and paracellular transport: an update. *Curr Opin Nephrol Hypertens* 2007; 16:459-64.
33. Heiskala M, Peterson P A, Yang Y. The roles of claudin superfamily proteins in paracellular transport. *Traffic* 2001; 2:93-8.
34. Hewitt K J, Agarwal R, Morin P J. The claudin gene family: expression in normal and neoplastic tissues. *BMC Cancer* 2006; 6:186.
35. Jovov B, Van Itallie C M, Shaheen N J, Carson J L, Gambling T M, Anderson J M, Orlando R C. Claudin-18: a dominant tight junction protein in Barrett's esophagus and likely contributor to its acid resistance. *Am J Physiol Gastrointest Liver Physiol* 2007; 293:G1106-13.
36. Hartsock A, Nelson W J. Adherens and tight junctions: structure, function and connections to the actin cytoskeleton. *Biochim Biophys Acta* 2008; 1778:660-9.
37. Niessen C M. Tight junctions/adherens junctions: basic structure and function. *J Invest Dermatol* 2007; 127:2525-32.
38. Ivanov A I, McCall I C, Babbin B, Samarin S N, Nusrat A, Parkos C A. Microtubules regulate disassembly of epithelial apical junctions. *BMC Cell Biol* 2006; 7:12.
39. Meng W, Mushika Y, Ichii T, Takeichi M. Anchorage of microtubule minus ends to adherens junctions regulates epithelial cell-cell contacts. *Cell* 2008; 135:948-59.
40. Gumbiner B, Stevenson B, Grimaldi A. The role of the cell adhesion molecule uvomorulin in the formation and maintenance of the epithelial junctional complex. *J Cell Biol* 1988; 107:1575-87.
41. Tobey N A, Argote C M, Hosseini S S, Orlando R C. Calcium-switch technique and junctional permeability in native rabbit esophageal epithelium. *Am J Physiol Gastrointest Liver Physiol* 2004; 286:G1042-9.
42. Garrod D R, Merritt A J, Nie Z. Desmosomal cadherins. *Curr Opin Cell Biol* 2002; 14:537-45.
43. Holthofer B, Windoffer R, Troyanovsky S, Leube R E. Structure and function of desmosomes. *Int Rev Cytol* 2007; 264:65-163.
44. Garrod D, Kimura T E. Hyper-adhesion: a new concept in cell-cell adhesion. *Biochem Soc Trans* 2008; 36:195-201.
45. Garrod D R, Berika M Y, Bardsley W F, Holmes D, Tabernero L. Hyper-adhesion in desmosomes: its regulation in wound healing and possible relationship to cadherin crystal structure. *J Cell Sci* 2005; 118:5743-54.
46. Salas P J, Misek D E, Vega-Salas D E, Gundersen D, Cereijido M, Rodriguez-Boulan E. Microtubules and actin filaments are not critically involved in the biogenesis of epithelial cell surface polarity. *J Cell Biol* 1986; 102:1853-67.
47. Cao W, Harnett K M, Cheng L, Kirber M T, Behar J, Biancani P. $H(2)O(2)$: a mediator of esophagitis-induced damage to calcium-release mechanisms in cat lower esophageal sphincter. *Am J Physiol Gastrointest Liver Physiol* 2005; 288:G1170-8.
48. Cheng L, Cao W, Fiocchi C, Behar J, Biancani P, Harnett K M. Platelet-activating factor and prostaglandin E2 impair esophageal ACh release in experimental esophagitis. *Am J Physiol Gastrointest Liver Physiol* 2005; 289:G418-28.
49. Cao W, Cheng L, Behar J, Fiocchi C, Biancani P, Harnett K M. Proinflammatory cytokines alter/reduce esophageal circular muscle contraction in experimental cat esophagitis. *Am J Physiol Gastrointest Liver Physiol* 2004; 287:G1131-9.
50. Cheng L H K, Cao W, Behar J, Bianicani P. Vanilloid receptor TRPV-1 induced PAF production mediates acid-induced esophageal inflammation. *Gastroenterology* 2006.
51. Rieder F, Cheng L, Harnett K M, Chak A, Cooper G S, Isenberg G, Ray M, Katz J A, Catanzaro A, O'Shea R, Post A B, Wong R, Sivak M V, McCormick T, Phillips M, West G A, Willis J E, Biancani P, Fiocchi C. Gastroesophageal reflux disease-associated esophagitis induces endogenous cytokine production leading to motor abnormalities. *Gastroenterology* 2007; 132:154-65.
52. Yoshida N. Inflammation and oxidative stress in gastroesophageal reflux disease. *J Clin Biochem Nutr* 2007; 40:13-23.
53. Banerjee B, Medda B K, Lazarova Z, Bansal N, Shaker R, Sengupta J N. Effect of reflux-induced inflammation on transient receptor potential vanilloid one (TRPV1) expression in primary sensory neurons innervating the oesophagus of rats. *Neurogastroenterol Motil* 2007; 19:681-91.
54. Tselepis C, Perry I, Dawson C, Hardy R, Darnton S J, McConkey C, Stuart R C, Wright N, Harrison R, Jankowski J A. Tumour necrosis factor-alpha in Barrett's oesophagus: a potential novel mechanism of action. *Oncogene* 2002; 21:6071-81.
55. Leone A K, Chun J A, Koehler C L, Caranto J, King J M. Effect of proinflammatory cytokines, tumor necrosis factor-alpha and interferon-gamma on epithelial barrier function and matrix metalloproteinase-9 in Madin Darby canine kidney cells. *Cell Physiol Biochem* 2007; 19:99-112.
56. Bruewer M, Samarin S, Nusrat A. Inflammatory bowel disease and the apical junctional complex. *Ann N Y Acad Sci* 2006; 1072:242-52.
57. Ma T Y, Boivin M A, Ye D, Pedram A, Said H M. Mechanism of TNF-{alpha} modulation of Caco-2 intestinal epithelial tight junction barrier: role of myosin light-chain kinase protein expression. *Am J Physiol Gastrointest Liver Physiol* 2005; 288:G422-30.
58. Arroyo M, Lanas A. NSAIDs-induced gastrointestinal damage. Review, *Minerva Gastroenterol Dietol* 2006; 52:249-59.
59. Bruewer M, Luegering A, Kucharzik T, Parkos C A, Madara J L, Hopkins A M, Nusrat A. Proinflammatory cytokines disrupt epithelial barrier function by apoptosis-independent mechanisms. *J Immunol* 2003; 171:6164-72.

60. Laukoetter M G, Bruewer M, Nusrat A. Regulation of the intestinal epithelial barrier by the apical junctional complex. *Curr Opin Gastroenterol* 2006; 22:85-9.
61. Salmo J A, Lehto V P, Myllarniemi H S, Kivilaakso E O. Morphological alterations in tryptic esophagitis: an experimental light microscopic and scanning and transmission electron microscopic study in rabbits. *J Surg Res* 1990; 49:14-7.
62. Salo J A, Kivilaakso E. Role of bile salts and trypsin in the pathogenesis of experimental alkaline esophagitis. *Surgery* 1983; 93:525-32.
63. Kono K, Takahashi A, Sugai H, Iizuka H, Fujii H. Trypsin activity and bile acid concentrations in the esophagus after distal gastrectomy. *Dig Dis Sci* 2006; 51:1159-64.
64. Imada T, Chen C, Hatori S, Shiozawa M, Rino Y. Effect of trypsin inhibitor on reflux oesophagitis after total gastrectomy in rats. *Eur J Surg* 1999; 165:1045-50.
65. Kono K, Takahashi A, Sugai H, Umekawa T, Yano T, Kamiyasu K, Teramatsu M, Fujii H. Oral trypsin inhibitor can improve reflux esophagitis after distal gastrectomy concomitant with decreased trypsin activity. *Am J Surg* 2005; 190:412-7.
66. Tobey N A, Gambling T M, Vanegas X C, Carson J L, Orlando R C. Physicochemical basis for dilated intercellular spaces in non-erosive acid-damaged rabbit esophageal epithelium. *Dis Esophagus* 2008.
67. Carlsson R, Fandriks L, Jonsson C, Lundell L, Orlando R C. Is the esophageal squamous epithelial barrier function impaired in patients with gastroesophageal reflux disease? *Scand J Gastroenterol* 1999; 34:454-8.
68. Soybel D I, Ashley S W, DeSchryver-Kecskemeti K, Cheung L Y. Effects of luminal hyperosmolality on cellular and paracellular ion transport pathways in necturus antrum. *Gastroenterology* 1987; 93:456-65.
69. Akhmanova A, Yap A S. Organizing junctions at the cell-cell interface. *Cell* 2008; 135:791-3.
70. Kee S H, Steinert P M. Microtubule disruption in keratinocytes induces cell-cell adhesion through activation of endogenous E-cadherin. *Mol Biol Cell* 2001; 12:1983-93.
71. Stehbens S J, Paterson A D, Crampton M S, Shewan A M, Ferguson C, Akhmanova A, Parton R G, Yap A S. Dynamic microtubules regulate the local concentration of E-cadherin at cell-cell contacts. *J Cell Sci* 2006; 119:1801-11.
72. Tousseyn T, Jorissen E, Reiss K, Hartmann D. (Make) stick and cut loose—disintegrin metalloproteases in development and disease. *Birth Defects Res C Embryo Today* 2006; 78:24-46.
73. Reiss K, Ludwig A, Saftig P. Breaking up the tie: disintegrin-like metalloproteinases as regulators of cell migration in inflammation and invasion. *Pharmacol Ther* 2006; 111:985-1006.
74. Maretzky T, Scholz F, Koten B, Proksch E, Saftig P, Reiss K. ADAM10-mediated E-cadherin release is regulated by proinflammatory cytokines and modulates keratinocyte cohesion in eczematous dermatitis. *J Invest Dermatol* 2008; 128:1737-46.
75. Marambaud P, Shioi J, Serban G, Georgakopoulos A, Sarner S, Nagy V, Baki L, Wen P, Efthimiopoulos S, Shao Z, Wisniewski T, Robakis N K. A presenilin-1/gamma-secretase cleavage releases the E-cadherin intracellular domain and regulates disassembly of adherens junctions. *Embo J* 2002; 21:1948-56.
76. Steinhusen U, Weiske J, Badock V, Tauber R, Bommert K, Huber O. Cleavage and shedding of E-cadherin after induction of apoptosis. *J Biol Chem* 2001; 276:4972-80.
77. Steinhusen U, Badock V, Bauer A, Behrens J, Wittman-Liebold B, Dorken B, Bommert K. Apoptosis-induced cleavage of beta-catenin by caspase-3 results in proteolytic fragments with reduced transactivation potential. *J Biol Chem* 2000; 275:16345-53.
78. Tobey N A, Argote C M, Vanegas X C, Barlow W, Orlando R C. Electrical parameters and ion species for active transport in human esophageal stratified squamous epithelium and Barrett's specialized columnar epithelium. *Am J Physiol Gastrointest Liver Physiol* 2007; 293:G264-70.
79. Asaoka D, Miwa H, Hirai S, Ohkawa A, Kurosawa A, Kawabe M, Hojo M, Nagahara A, Minoo T, Ohkura R, Ohkusa T, Sato N. Altered localization and expression of tight junction proteins in a rat model with chronic acid reflux esophagitis. *J Gastroenterol* 2005; 40:781-90.
80. Orlando R C. Reflux esophagitis. In: Yamada T, Alpers D, Owyang C, Powell D, Laine L, eds. *Textbook of Gastroenterology*. $3^{rd}$ ed. Philadelphia: JB Lippincott Williams & Wilkins, 1999:1235-1263.
81. Fass R, Shapiro M, Dekel R, Sewell J. Systematic review: proton-pump inhibitor failure in gastro-oesophageal reflux disease—where next? *Aliment Pharmacol Ther* 2005; 22:79-94.
82. van Malenstein H, Farre R, Sifrim D. Esophageal dilated intercellular spaces (DIS) and nonerosive reflux disease. *Am J Gastroenterol* 2008; 103:1021-8.
83. Mueller S, Neureiter D, Aigner T, Stolte M. Comparison of histological parameters for the diagnosis of eosinophilic oesophagitis versus gastro-oesophageal reflux disease on oesophageal biopsy material. *Histopathology* 2008; 53:676-84.
84. Rodrigo S, Abboud G, Oh D, DeMeester S R, Hagen J, Lipham J, DeMeester T R, Chandrasoma P. High intraepithelial eosinophil counts in esophageal squamous epithelium are not specific for eosinophilic esophagitis in adults. *Am J Gastroenterol* 2008; 103:435-42.
85. Spechler S J, Genta R M, Souza R F. Thoughts on the complex relationship between gastroesophageal reflux disease and eosinophilic esophagitis. *Am J Gastroenterol* 2007; 102:1301-6.
86. Long J D, Marten E, Tobey N A, Orlando R C. Effects of luminal hypertonicity on rabbit esophageal epithelium. *Am J Physiol* 1997; 273:G647-54.
87. Pedrazzani C, Caruso S, Corso G, Marrelli D, Neri A, Berardi A, Roviello F. Influence of age on soluble E-cadherin serum levels prevents its utility as a disease marker in gastric cancer patients. *Scand J Gastroenterol* 2008; 43:765-6.
88. Chan A O, Lam S K, Chu K M, Lam C M, Kwok E, Leung S Y, Yuen S T, Law S Y, Hui W M, Lai K C, Wong C Y, Hu H C, Lai C L, Wong J. Soluble E-cadherin is a valid prognostic marker in gastric carcinoma. *Gut* 2001; 48:808-11.
89. De Wever O, Derycke L, Hendrix A, De Meerleer G, Godeau F, Depypere H, Bracke M. Soluble cadherins as cancer biomarkers. *Clin Exp Metastasis* 2007; 24:685-97.
90. Shirahama S, Furukawa F, Wakita H, Takigawa M. E- and P-cadherin expression in tumor tissues and soluble E-cadherin levels in sera of patients with skin cancer. *J Dermatol Sci* 1996; 13:30-6.
91. Tobey N A, Koves G, Orlando R C. Human esophageal epithelial cells possess an Na+/H+ exchanger for H+ extrusion. *Am J Gastroenterol* 1998; 93:2075-81.
92. Tobey N A, Reddy S P, Keku T O, Cragoe E J, Jr., Orlando R C. Studies of pHi in rabbit esophageal basal and squamous epithelial cells in culture. *Gastroenterology* 1992; 103:830-9.

93. Tinkle C L, Pasolli H A, Stokes N, Fuchs E. New insights into cadherin function in epidermal sheet formation and maintenance of tissue integrity. *Proc Natl Acad Sci USA* 2008; 105:15405-10.
94. Makagiansar I T, Avery M, Hu Y, Audus K L, Siahaan T J. Improving the selectivity of HAV-peptides in modulating E-cadherin-E-cadherin interactions in the intercellular junction of MDCK cell monolayers. *Pharm Res* 2001; 18:446-53.
95. Noe V, Willems J, Vandekerckhove J, Roy F V, Bruyneel E, Mareel M. Inhibition of adhesion and induction of epithelial cell invasion by HAV-containing E-cadherin-specific peptides. *J Cell Sci* 1999; 112 (Pt 1): 127-35.
96. Noe V, Fingleton B, Jacobs K, Crawford H C, Vermeulen S, Steelant W, Bruyneel E, Matrisian L M, Mareel M. Release of an invasion promoter E-cadherin fragment by matrilysin and stromelysin-1. *J Cell Sci* 2001; 114:111-118.
97. Nollet F, Berx G, van Roy F. The role of the E-cadherin/catenin adhesion complex in the development and progression of cancer. *Mol Cell Biol Res Commun* 1999; 2:77-85.
98. Ferber E C, Kajita M, Wadlow A, Tobiansky L, Niessen C, Ariga H, Daniel J, Fujita Y. A role for the cleaved cytoplasmic domain of E-cadherin in the nucleus. *J Biol Chem* 2008; 283:12691-700.
99. Maretzky T, Reiss K, Ludwig A, Buchholz J, Scholz F, Proksch E, de Strooper B, Hartmann D, Saftig P. ADAM10 mediates E-cadherin shedding and regulates epithelial cell-cell adhesion, migration, and beta-catenin translocation. *Proc Natl Acad Sci USA* 2005; 102:9182-7.
100. Sareddy G R, Challa S, Panigrahi M, Babu P P. Wnt/beta-catenin/Tcf Signaling Pathway Activation in Malignant Progression of Rat Gliomas Induced by Transplacental N-Ethyl-N-Nitrosourea Exposure. *Neurochem Res* 2009.
101. Barker N. The canonical Wnt/beta-catenin signalling pathway. *Methods Mol Biol* 2008; 468:5-15.
102. Rogers S L, Gelfand V I. Membrane trafficking, organelle transport, and the cytoskeleton. *Curr Opin Cell Biol* 2000; 12:57-62.
103. Miyoshi J, Takai Y. Structural and functional associations of apical junctions with cytoskeleton. *Biochim Biophys Acta* 2008; 1778:670-91.
104. Goldstein J L, Schmidt L N, Al-Bazzaz F J, Layden T J. Effects of taurine-conjugated bile salts on ionic transport of the rabbit esophageal mucosa. *Am J Physiol* 1986; 251: G688-94.
105. Nehra D, Howell P, Williams C P, Pye J K, Beynon J. Toxic bile acids in gastro-oesophageal reflux disease: influence of gastric acidity. *Gut* 1999; 44:598-602.
106. Dean B B, Gano A D, Jr., Knight K, Ofman J J, Fass R. Effectiveness of proton pump inhibitors in nonerosive reflux disease. *Clin Gastroenterol Hepatol* 2004; 2:656-64.
107. Long J D, Orlando R C. Nonerosive reflux disease. *Minerva Gastroenterol Dietol. Volume* 53, 2007:127-41,
108. Fass R, Gasiorowska A. Refractory GERD: what is it? *Curr Gastroenterol Rep* 2008; 10:252-7.
109. Pehlivanov N, Liu J, Mittal R K. Sustained esophageal contraction: a motor correlate of heartburn symptom. *Am J Physiol Gastrointest Liver Physiol* 2001; 281:G743-51.
110. Bhalla V, Liu J, Puckett J L, Mittal R K. Symptom hypersensitivity to acid infusion is associated with hypersensitivity of esophageal contractility. *Am J Physiol Gastrointest Liver Physiol* 2004; 287:G65-71.
111, Boussadia O, S. K, A. H, V. D, R. K, E-cadherin is a survival factor for the lactating mouse mammary gland. *Mech Dev* 2002; 115:53-62.
112. Rock J R, Onaitis M W, Rawlins E L, Lu Y, Clark C P, Xue Y, Randell S H, Hogan B L, Basal cells as stem cells of the mouse trachea and human airway epithelium. *Proc Natl Acad Sci USA* 2009; 106:12771-5.
113. Que J, Wilm B, Hasegawa H, Wang F, Bader D, Hogan B L. Mesothelium contributes to vascular smooth muscle and mesenchyme during lung development. *Proc Natl Acad Sci U S A* 2008; 105:16626-30.
114. Que J, Luo X, Schwartz R J, Hogan B L. Multiple roles for Sox2 in the developing and adult mouse trachea. *Development* 2009; 136:1899-907.
115. Holmes J L, Van Itallie C M, Rasmussen J E, Anderson J M. Claudin profiling in the mouse during postnatal intestinal development and along the gastrointestinal tract reveals complex expression patterns. *Gene Expr Patterns* 2006; 6:581-8.
116. Matsuyoshi N, Tanaka T, Toda K, Okamoto H, Furukawa F, Imamura S, Soluble E-cadherin: a novel cutaneous disease marker. *Br J Dermatol* 1995; 132:745-9.
117. Crawford H C, Dempsey P J, Brown G, Adam L, Moss M L. ADAM10 as a therapeutic target for cancer and inflammation. *Curr Pharm Des* 2009; 15:2288-99.
118, Derycke L, De Wever O, Stove V, Vanhoecke B, Delanghe J, Depypere H, Bracke M. Soluble N-cadherin in human biological fluids. *Int J Cancer* 2006; 119:2895-900.
119. Frank C F, Hostetter M K. Cleavage of E-cadherin: a mechanism for disruption of the intestinal epithelial barrier by *Candida albicans. Transl Res* 2007; 149:211-22

That which is claimed is:

1. A method of monitoring the healing of reflux esophagitis in a subject comprising:
- detecting the amount of E-cadherin N-terminal fragments (NTF) in a first blood sample from a subject prior to beginning treatment for reflux esophagitis;
- detecting the amount of E-cadherin NTF in a second blood sample from said subject at a time point after treatment for reflux esophagitis has begun; and
- comparing the amount of E-cadherin NTF in said first and second blood samples,
- wherein a decrease in the amount of E-cadherin NTF between the first blood sample and the second blood sample indicates the healing of reflux esophagitis in said subject.

2. The method of claim 1, wherein the subject is human.

3. The method of claim 1, wherein the detecting comprises flow cytometry, affinity purification, immunocytochemistry, Western blots, immunoblots, immunoprecipitation, immunohistochemistry, immunofluorescence, enzyme-linked immunosorbant assays (ELISA), radioimmunoassay, densitometry, column chromatography, or any combination thereof.

* * * * *

UNITED STATES PATENT AND TRADEMARK OFFICE
CERTIFICATE OF CORRECTION

PATENT NO. : 8,679,766 B2  Page 1 of 1
APPLICATION NO. : 13/305790
DATED : March 25, 2014
INVENTOR(S) : Orlando et al.

It is certified that error appears in the above-identified patent and that said Letters Patent is hereby corrected as shown below:

In the Specification:
Column 8, Line 17: Delete "diagnosis:" Insert -- diagnosis. --

Column 34, Lines 1 and 2: Delete "KRT5-CreER;E-cadherin (E-cad$^{\Delta/\Delta}$"
Insert -- *KRT5-CreER;E-cadherin*$^{flax/flax}$ (E-*cad*$^{\Delta/\Delta}$) --

Signed and Sealed this
Third Day of February, 2015

Michelle K. Lee
*Deputy Director of the United States Patent and Trademark Office*